US010946012B2

(12) United States Patent
Sebti et al.

(10) Patent No.: US 10,946,012 B2
(45) Date of Patent: Mar. 16, 2021

(54) METHODS FOR INDUCING TUMOR REGRESSION, INHIBITING TUMOR GROWTH, AND INDUCING APOPTOSIS IN BREAST TUMORS WITH GERANYLGERANYLTRANSFERASE I INHIBITORS

(75) Inventors: Said M. Sebti, Tampa, FL (US); Andrew D. Hamilton, Oxford (GB)

(73) Assignees: H. Lee Moffitt Cancer Center and Research Institute, Inc., Tampa, FL (US); Yale University, New Haven, CT (US)

( * ) Notice: Subject to any disclaimer, the term of this patent is extended or adjusted under 35 U.S.C. 154(b) by 198 days.

(21) Appl. No.: 13/194,022

(22) Filed: Jul. 29, 2011

(65) Prior Publication Data

US 2012/0035184 A1 Feb. 9, 2012

Related U.S. Application Data

(63) Continuation of application No. PCT/US2010/022498, filed on Jan. 29, 2010.

(60) Provisional application No. 61/148,244, filed on Jan. 29, 2009.

(51) Int. Cl.
*A61K 31/496* (2006.01)

(52) U.S. Cl.
CPC .................. *A61K 31/496* (2013.01)

(58) Field of Classification Search
None
See application file for complete search history.

(56) References Cited

U.S. PATENT DOCUMENTS 6,180,333 B1 * 1/2001 Giordano ........................ 435/4
7,763,620 B2 * 7/2010 Hamilton ............. C07D 241/08
514/255.02

FOREIGN PATENT DOCUMENTS

WO WO 1998/33450 A1 * 8/1998
WO WO 2003/017939 A2 * 6/2003

OTHER PUBLICATIONS

Jacob LS. The National Medical Series for Independent Study: Pharmacology (4th Edition). Williams and Wilkins; 1996. pp. 1-13.*
Fred Hutchinson Cancer Research Center [Online]. "The Predictive Power of p27". [Retrieved Sep. 4, 2013]. Retrieved from the Internet: <URL: http://www.fhcrc.org/en/news/center-news/2006/12/predictive-power.html>. pp. 1-2. 2006.*
Patel et al. "RKI-1447 Is a Potent Inhibitor of the Rho-Associated ROCK Kinases with Anti-Invasive and Antitumor Activities in Breast Cancer". Cancer Res, 2012; 72(19):5025-5034.*
Berndt et al. "Targeting Protein Prenylation for Cancer Therapy". Nature Reviews, 2011; 11:775-791.*
Lu et al. "In Vivo Antitumor Effect of a Novel Inhibitor of Protein Geranylgeranyltransferase-I". Mol Cancer Ther, 2009; 8(5):1218-1226.*
Holstein et al. "Is There a Future for Prenyltransferase Inhibitors in Cancer Therapy". Current Opinion in Pharmacology, 2012; 12:704-709.*
Sun et al. "Geranylgeranyltransferase I Inhibitor GGTI-2154 Induces Breast Carcinoma Apoptosis and Tumor Regression in H-Ras Transgenic Mice". Cancer Res, 2003; 63(24):8922-8929.*
Shen et al. "Farnesyltransferase and Geranylgeranyltransferase I: Structures, Mechanism, Inhibitors and Molecular Modeling". Drug Discovery Today, 2015; 20(2):267-276.*
Clarke RB. "p27Kip1 Phosphorylation by PKB/Akt Leads to Poor Breast Cancer Prognosis". Breast Cancer Res, 2003; 5:162-163.*
Frei et al. [Online]. "Chapter 40: Principles of Dose, Schedule, and Combination Chemotherapy" from Holland-Frei Cancer Medicine (Fifth Edition). [Retrieved Jan. 18, 2013]. Retrieved from the Internet: <URL: http://www.ncbi.nlm.nih.gov/books/NBK20768/?report=printable>.*
Kazi et al. "The Geranylgeranyltransferase I Inhibitor GGTI-2418/2417 Blocks Cdk2-Dependent p27Kip1 Phosphorylation on Thr187 and Accumulates p27Kip1 in the Nucleus: Implications for Breast Cancer Therapy". Proc Am Assoc Cancer Res. Apr. 18-22, 2009, Abstract #3648. (Year: 2009).*
Montagnoli et al. 1999. "Ubquitination of p27 is Regulated by Cdk-Dependent Phosphorylation and Trimeric Complex Formation." Genes & Development. vol. 13. pp. 1181-1189.
Kazi et al. 2009. "Blockade of Protein Geranylgeranylation Inhibits Cdk2-Dependent p27(Kip1) Phosphorylation on Thr187 and Accumulates p27(Kip1) in the Nucleus: Implications for Breast Cancer Therapy." Molecular and Cellular Biology. vol. 29. No. 8. pp. 2254-2263.
Reuveni et al. 2003. "The Inhibition of Ras Farnesylation Leads to an Increase in p27(Kip1) and G1 Cell Cycle Arrest." Eur. J. Biochem. vol. 270. pp. 2759-2772.
Sun et al. 1999. "The Geranylgeranyltransferase I Inhibitor GGTI-298 Induces Hypophosphorylation of Retinoblastoma and Partner Switching of Cyclin-Dependent Kinase Inhibitors." The Journal of Biological Chemistry. vol. 274. No. 11. pp. 6930-6934.
Carloni et al. 2005. "Farnesyltransferase Inhibitor, ABT-100, Is a Potent Liver Cancer Chemopreventive Agent." Clin. Cancer Res. vol. 11. No. 11. pp. 4266-4274.
Falsetti et al. 2007. "Geranylgeranyltransferase I Inhibitors Target RalB to Inhibit Anchorage-Dependent Growth and Induce Apoptosis and RalA to Inhibit Anchorage-Independent Growth." Molecular and Cellular Biology. vol. 27. No. 22. pp. 8003-8014.

(Continued)

*Primary Examiner* — Leslie A. Royds Draper
(74) *Attorney, Agent, or Firm* — Thomas| Horstemeyer LLP

(57) ABSTRACT

Methods of inducing tumor regression, inhibiting tumor growth, and inducing apoptosis with selective peptidomimetic inhibitors of geranylgeranyltransferase I (GGTase I), are provided. In one aspect, GGTI-2418 and its methylester GGTI-2417, increase levels of the cyclin-dependent kinase (Cdk) inhibitor p27$^{Kip1}$ and induce breast tumor regression in vivo. In another aspect, GGTI-2417 inhibits the Cdk2-mediated phosphorylation of p27$^{Kip1}$ at Thr187 and accumulates p27$^{Kip1}$ in the nucleus.

4 Claims, 25 Drawing Sheets

Specification includes a Sequence Listing.

(56) References Cited

OTHER PUBLICATIONS

Blaskovich et al. 2004. "Geranylgeranyltransferase I Inhibitors Induce p27 Accumulation and G1 Arrest in Human Breast Cancer Cell Lines Independently of Rb Status and Expression Levels of Erb1, 2, 3 and 4." Proc. Amer. Assoc. Cancer Res. vol. 45. Abstract.

Sun et al. 2003. "Geranylgeranyltransferase I Inhibitor GGTI-2154 Induces Breast Carcinoma Apoptosis and Tumor Regression in H-Ras Transgenic Mice." Cancer Research. vol. 63. pp. 8922-8929.

Adnane et al. 1998. "p21(WAF1/CIP1) is Upregulated by the Geranylgeranyltransferase I Inhibitor GGTI-298 Through a Transforming Growth Factor Beta- and Sp1-Responsive Element: Involvement of the Small GTPase RhoA." Mol. Cell. Biol. vol. 18. No. 12. pp. 6962-6970.

Bagui et al. 2000. "Analysis of Cyclin D3-cdk4 Complexes in Fibroblasts Expressing and Lacking p27(kip1) and p21 (cip1)." Mol. Cell. Biol. vol. 20. No. 23. pp. 8748-8757.

Blain et al. 2003. "p27 as a Target for Cancer Therapeutics." Cancer Cell. vol. 3. pp. 111-115.

Besson et al. 2007. "Discovery of an Oncogenic Activity in p27(Kip1) that Causes Stem Cell Expansion and a Multiple Tumor Phenotype." Genes Dev. vol. 21. pp. 1731-1746.

Borriello et al. 2007. "p27(Kip1) Metabolism: a Fascinating Labyrinth." Cell Cycle. vol. 6. pp. 1053-1061.

Burbelo et al. 2004. Altered Rho GTPase Signaling Pathways in Breast Cancer Cells. Breast Cancer Res. Treat. vol. 84. pp. 43-48.

Cariou et al. 1998. Prognostic Implications of Expression of the Cell Cycle Inhibitor Protein p27(Kip1). Breast Cancer Res. Treat. vol. 52. pp. 29-41.

Zhang et al. 1996. Protein prenylation: molecular mechanisms and functional consequences. Annu. Rev. Biochem. vol. 65. pp. 241-269.

Wu et al. 2006. Reduction of cytosolic p27Kip1 inhibits cancer cell motility, survival, and tumorigenicity. Cancer Res. vol. 66. pp. 2162-2172.

Weber et al. 1997. Ras-stimulated extracellular signal-related kinase 1 and RhoA activities coordinate platelet-derived growth factor-induced G1 progression through the independent regulation of cyclin D1 and p27(kip1). J. Biol. Chem. vol. 272. No. 52. pp. 32966-32971.

Walker et al. 2005. Targeting Ras and Rho GTPases as opportunities for cancer therapeutics. Curr. Opin. Genet. Dev. vol. 15. pp. 62-68.

Vogt et al. 1997. The geranylgeranyltransferase-I inhibitor GGTI-298 arrests human tumor cells in G0/G1 and induces p21(WAF1/CIP1/SDI1) in a p53-independent manner. J. Biol. Chem. vol. 272. No. 43. pp. 27224-27229.

Viglietto et al. 2002. Cytoplasmic relocalization and inhibition of the cyclin-dependent kinase inhibitor p27Kip1 by PKB/Akt-mediated phosphorylation in breast cancer. Nat. Med. vol. 8. No. 10. pp. 1136-1144.

Vargo-Gogola et al. 2007. Modelling breast cancer: one size does not fit all. Nat. Rev. Cancer. vol. 7.pp. 659-672.

Sun et al. 1999. The geranylgeranyltransferase I inhibitor GGTI-298 induces hypophosphorylation of retinoblastoma and partner switching of cyclin-dependent kinase inhibitors. A potential mechanism for GGTI-298 antitumor activity. J. Biol. Chem. vol. 274. No. 11. pp. 6930-6934.

Sun et al. 1999. Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. Cancer Res. vol. 59. pp. 4919-4926.

Sjogren et al. 2007. GGTase-1 deficiency reduces tumor formation and improves survival in mice with K-Ras-induced lung cancer. J. Clin. Investig. vol. 117. No. 5. pp. 1294-1304.

Shin et al. 2002. PKB/Akt mediates cell-cycle progression by phosphorylation of p27(Kip1) at threonine 157 and modulation of its cellular localization. Nat. Med. vol. 8. No. 10. pp. 1145-1152.

Sherr et al. 1999. CDK inhibitors: positive and negative regulators of G1-phase progression. Genes Dev. vol. 13. pp. 1501-1512.

Sebti. 2005. Protein farnesylation: implications for normal physiology, malignant transformation, and cancer therapy. Cancer Cell. vol. 7. pp. 297-300.

Sebti et al. 2003. Opinion: searching for the elusive targets of farnesyltransferase inhibitors. Nat. Rev. Cancer. vol. 3. pp. 945-951.

Sebti et al. 2000. Farnesyltransferase and geranylgeranyltransferase I inhibitors and cancer therapy: lessons from mechanism and bench-to-bedside translational studies. Oncogene. vol. 19. pp. 6584-6593.

Ridley. 2004. Rho proteins and cancer. Breast Cancer Res. Treat. vol. 84. pp. 13-19.

Peng et al. 2006. Synthesis and evaluation of potent, highly-selective, 3-aryl-piperazinone inhibitors of protein geranylgeranyltransferase-I. Org. Biomol. Chem. vol. 4. pp. 1768-1784.

Min et al. 2004. Cytoplasmic mislocalization of p27Kip1 protein is associated with constitutive phosphorylation of Akt or protein kinase B and poor prognosis in acute myelogenous leukemia. Cancer Res. vol. 64. pp. 5225-5231.

Liang et al. 2002. PKB/Akt phosphorylates p27, impairs nuclear import of p27 and opposes p27-mediated G1 arrest. Nat. Med. vol. 8. No. 10. pp. 1153-1160.

Lerner et al. 1995. Disruption of oncogenic K-Ras4B processing and signaling by a potent geranylgeranyltransferase I inhibitor. J. Biol. Chem. vol. 270. No. 45. pp. 26770-26773.

Lerner et al. 1995. Ras CAAX peptidomimetic FTI-277 selectively blocks oncogenic Ras signaling by inducing cytoplasmic accumulation of inactive Ras-Raf complexes. J. Biol. Chem. vol. 270. No. 45. pp. 26802-26806.

Le et al. 2005. HER2-targeting antibodies modulate the cyclin-dependent kinase inhibitor p27Kip1 via multiple signaling pathways. Cell Cycle. vol. 4. No. 1. pp. 87-95.

Kossatz et al. 2006. C-terminal phosphorylation controls the stability and function of p27Kip1. EMBO J. vol. 25. No. 21. pp. 5159-5170.

Kaufmann et al. 1993. Specific proteolytic cleavage of poly(ADP-ribose) polymerase: an early marker of chemotherapy-induced apoptosis. Cancer Res. vol. 53. pp. 3976-3985.

Kamura et al. 2004. Cytoplasmic ubiquitin ligase KPC regulates proteolysis of p27(Kip1) at G1 phase. Nat. Cell Biol. vol. 6. No. 12. pp. 1229-1235.

Ishida et al. 2000. Phosphorylation at serine 10, a major phosphorylation site of p27(Kip1), increases its protein stability. J. Biol. Chem. vol. 275. No. 33. pp. 25146-25154.

Ishida et al. 2002. Phosphorylation of p27Kip1 on serine 10 is required for its binding to CRM1 and nuclear export. J. Biol. Chem. vol. 277. No. 17. pp. 14355-14358.

Hirai et al. 1997. Geranylgeranylated Rho small GTPase(s) are essential for the degradation of p27Kip1 and facilitate the progression from G1 to S phase in growth stimulated rat FRTL-5 cells. J. Biol. Chem. vol. 272. No. 1. pp. 13-16.

Hara et al. 2001. Degradation of p27Kip1 at the G0-G1 transition mediated by a Skp2-independent ubiquitination pathway. J. Biol. Chem. vol. 276. No. 52. pp. 48937-48943.

Han et al. 1999. Reduced expression of p27Kip1 protein is associated with poor clinical outcome of breast cancer patients treated with systemic chemotherapy and is linked to cell proliferation and differentiation. Breast Cancer Res. Treat. vol. 55. pp. 161-167.

Grimmler et al. 2007. Cdk-inhibitory activity and stability of p27Kip1 are directly regulated by oncogenic tyrosine kinases. Cell vol. 128. pp. 269-280.

Gelb et al. 2006. Therapeutic intervention based on protein prenylation and associated modifications. Nat. Chem. Biol. vol. 2. No. 10. pp. 518-528.

Fritz et al. 2006. Rho GTPases: promising cellular targets for novel anticancer drugs. Curr. Cancer Drug Targets vol. 6. No. 10. pp. 1-14.

Drexler. 2003. The role of p27Kip1 in proteasome inhibitor induced apoptosis. Cell Cycle. vol. 2. pp. 438-441.

Denicourt. 2007. Relocalized p27Kip1 tumor suppressor functions as a cytoplasmic metastatic oncogene in melanoma. Cancer Res. vol. 67. pp. 9238-9243.

(56) References Cited

OTHER PUBLICATIONS

Dan et al. 2004. Phosphatidylinositol-3-OH kinase/AKT and survivin pathways as critical targets for geranylgeranyltransferase I inhibitor-induced apoptosis. Oncogene. vol. 23. pp. 706-715.
Croft et al. 2006. The Rho GTPase effector ROCK regulates cyclin A, cyclin D1, and p27Kip1 levels by distinct mechanisms. Mol. Cell. Biol. vol. 26. No. 12. pp. 4612-4627.
Coleman et al. 2004. RAS and RHO GTPases in G1-phase cell-cycle regulation. Nat. Rev. Mol. Cell Biol. vol. 5. pp. 355-366.
Coleman et al. 2006. Stability of p21Waf1/Cip1 CDK inhibitor protein is responsive to RhoA-mediated regulation of the actin cytoskeleton. Oncogene. vol. 25. pp. 2708-2716.
Chu et al. 2008. The Cdk inhibitor p27 in human cancer: prognostic potential and relevance to anticancer therapy. Nat. Rev. Cancer. vol. 8. pp. 253-267.
Chu et al. 2007. p27 phosphorylation by Src regulates inhibition of cyclin E-cdk2. Cell. vol. 128. pp. 281-294.
Catzavelos et al. 1997. Decreased levels of the cell-cycle inhibitor p27Kip1 protein: prognostic implications in primary breast cancer. Nat. Med. vol. 3. No. 2. pp. 227-230.
Badache et al. 2006. The ErbB2 signaling network as a target for breast cancer therapy. J. Mammary Gland Biol. Neoplasia. vol. 11. pp. 13-25.
Alkarain et al. 2004. p27 deregulation in breast cancer: prognostic significance and implications for therapy. J. Mammary Gland Biol. Neoplasia. vol. 9. No. 1. pp. 67-80.
Barbareschi. 1999. p27 expression, a cyclin dependent kinase inhibitor in breast carcinoma. Adv. Clin. Pathol. vol. 3. pp. 119-127.
Hu et al. 1999. RhoA stimulates p27(Kip) degradation through its regulation of cyclin E/CDK2 activity. J. Biol. Chem. vol. 274. No. 6. pp. 3396-3401.
Of mice and men—are mice relevant models for human disease? Outcomes of the European Commission workshop 'Are mice relevant models for human disease?' held in London, UK, on May 21, 2010. pp. 1-10.
Anna Fantozzi, et al., Review: Mouse Models of Breast Cancer Metastasis. Breast Cancer Research, 2006, vol. 8, Issue 4, pp. 1-11.
Tracy Vargo-Gogola, et al., Modelling Breast Cancer: one size does not fit all. Nature Reviews; Cancer, vol. 7, Sep. 2007. pp. 659-672.
Piyush B. Gupta, et al., Disease Models of Breast Cancer. Drug Discovery Today: Disease Models, vol. I, No. I, 2004, pp. 9-16.
Elizabeth Lorns, et al., A New Mouse Model for the Study of Human Breast Cancer Metastasis. PLOS ONE; Human Breast Cancer Metastasis Mouse Model, vol. 7, Issue 10, Oct. 2012. pp. 1-8.
Ann Richmond, et al., Mouse Xenograft Models vs GEM Models for Human Cancer Therapeutics. Dis. Model Mech. vol. 1, Issue 2-3, Sep.-Oct. 2008. pp. 78-82. Accessed by web address: http://www.ncbi.nlm.nih.gov/pmc/articles/pmc/articles/pmc2562196/?report=printable. Accessed on Jun. 27, 2013.
Paolo Vineis, et al., A darwinian perspective: right premises, questionable conclusion. A commentary on Niall Shanks and Rebecca Pyles "Evolution and medicine: the long reach of "Dr. Darwin"". Philosophy, Ethics, and Humanites in Medicine; BioMed Central. vol. 3, Issue 6, 2008. pp. 1-3.
Besson, et al., "Discovery of an oncogenic activity in $p27^{Kip1}$ that causes stem cell expansion and a multiple tumor phenotype", Genes & Development 21:1731-1746.
Robert B. Clarke, "$p27^{KIP1}$ phosphorylation by PKB/Akt leads to poor breast cancer prognosis", Breast Cancer Research, vol. 5, No. 3.
Gomez del Pulgar, et al., "Rho GTPase expression in tumourigenesis: evidence for a significant link", BioEssays 27:602-613.
Hagen, et al., "Silencing CDK4 radiosensitizes breast cancer cells by promoting apoptisis", Cell division 2013, 8:10.
Hayashi, et al., "High cyclin E and low p27/Kip1 expressions are potentially poor prognostic factors in lung adenocarcinoma patients", Lung Cancer 34, pp. 59-65.
Hidaka, et al., "The Combination of Low Cytoplasmic and High Nuclear Expression of p27 Predicts a Better Prognosis in High-grade Astrocytoma", Anticancer Research, 29: pp. 597-604.
Holliday, et al., "Choosing the right cell line for breast cancer research", Breast Cancer Research, 2011, 13:215.
Jeong, et al., "Neuregulin-1 induces cancer stem cell characteristics in breast cancer cell lines", Oncology Reports 32:1218-1224.
Khan, et al., "Microbead Arrays for the Analysis of ErbB Receptor Tyrosine Kinase Activation and Dimerization in Breast Cancer Cells", ASSAY and Drug Development Technologies, vol. 8, No. 1.
Li, et al., "Biological Correlates of p27 Compartmental Expression in Prostate Cancer", The Journal of Urology, vol. 175, pp. 528-532.
Lin, et al., "Association of cytoplasmic p27 expression with an unfavorable response to cisplatin-based chemotherapy and poor outcomes in non-small cell lung cancer", Tumor Biol., 37:4017-4023.
Loda, et al., "Increased proteasome-dependent degradation of the cyclin-dependent kinase inhibitor p27 in aggressive colorectal carcinomas", Nature Medicine, vol. 3, No. 2, pp. 231-234.
Mudvari, et al., "Genomic Insights into Triple-Negative and HER2-Positive Breast Cancers Using Isogenic Model Systems", PLOS One, 2013, vol. 8, Issue 9 e74993.
Philipp-Staheli, et al., "$p27^{Kip1}$: Regulation and Function of a Haploinsufficient Tumor Suppressor and Its Misregulation in Cancer", Expiremental Cell Research 264, pp. 148-168.
Roy, et al., "Increased Cytoplasmic Localization of $p27^{kip1}$ and Its Modulation of RhoA Activity During Progression of Chronic Myeloid Leukemia", PLOS One vol. 8, Issue 10 e76527.
Sgambato, et al., "Loss of $P27^{Kip1}$ Expression Correlates with Tumor Grade and with Reduced Disease-free Survival in Primary Superficial Bladder Cancers ", Cancer Research 59, pp. 3245-3250.
Slingerland, et al., "Regulation of the Cdk Inhibitor p27 and Its Deregulation in Cancer", Journal of Cellular Physiology, 183: 10-17.
Subik, et al., "The Expression Patters of ER, PR, HER2, CK5/6, EGFR, Ki-67 and AR by Immunohistochemical Analysis in Breast Cancer Cell Lines", Breast Cancer: Basic and Clinical Research, 2010:4 35-41.
Tsukamoto, et al., "Reduced expression of cell-cycle regulator $p27^{Kip1}$ correlates with a shortened survival in non-small cell lung cancer", Lung Cancer 34:83-90.
Watanabe, et al., "Functional Analysis of Secreted Caveolin-1 in Mouse Models of Prostate Cancer Progression", Mol Cancer Res 7(9), pp. 1146-1455.
Wen, et al., "Promotion of cytoplasmic mislocalization of p27 by *Helicobacter pylori* in gastric cancer", Oncogene, 31: 1771-1780.

\* cited by examiner

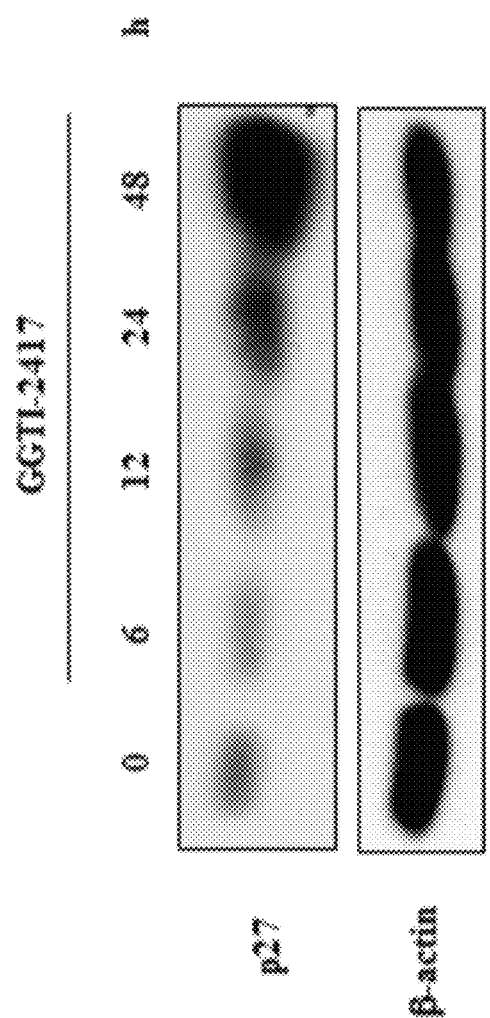

| GGTI-2417 (µM) | 0 | 1 | 10 | 30 | 50 | 100 |
|---|---|---|---|---|---|---|
| % $G_0/G_1$ | 51 | 64 | 74 | 75 | 78 | 80 |
| % S | 28 | 22 | 12 | 10 | 8 | 7 |
| % $G_2/M$ | 21 | 14 | 13 | 16 | 14 | 13 |

GGTI-2417 induces G0/G1 phase accumulation.

FIG. 6

Effects of 50 µM GGTI-2417 on proliferation, cell death, and cell cycle distribution

| CGTI-2417 | MDA-MB-468 | | MDA-MB-231 | | SK-Br-3 | | BT-474 | |
|---|---|---|---|---|---|---|---|---|
| | − | + | − | + | − | + | − | + |
| % Proliferation | 100 | 52 ± 5.5 | 100 | 30 ± 8.2 | 100 | 75 ± 5.5 | 100 | 42 ± 12 |
| % G₀/G₁ | 49 ± 9.3 | 75 ± 4.7 | 62 ± 8.7 | 86 ± 8.1 | 62 ± 4.9 | 69 ± 4.2 | 69 ± 8.6 | 78 ± 8.7 |
| % Cell Death | 7 ± 4 | 21 ± 10 | 18 ± 7 | 68 ± 6 | 9 ± 2 | 26 ± 8 | 15 ± 3 | 32 ± 5 |

FIG. 7

GGTI-2418 causes breast tumor regression *in vivo*

| Tumor # | To* (mm³) | Ts* (mm³) | % Tumor Regression |
|---|---|---|---|
| 1 | 1,124 | 0 | 100 |
| 2 | 1,863 | 406 | 78 |
| 3 | 1,492 | 506 | 66 |
| 4 | 1,204 | 430 | 64 |
| 5 | 1,843 | 437 | 76 |
| 6 | 1,355 | 411 | 70 |
| 7 | 2,186 | 915 | 58 |
| 8 | 1,642 | 799 | 51 |
| 9 | 1,187 | 732 | 38 |
| 10 | 1,287 | 599 | 53 |
| 11 | 1,573 | 594 | 62 |
| 12 | 1,424 | 638 | 55 |
| 13 | 3,903 | 2312 | 41 |
| 14 | 1,670 | 802 | 52 |
| 15 | 1,604 | 691 | 57 |
| 16 | 1,124 | 741 | 34 |
| 17 | 818 | 336 | 59 |
| Average ± standard error = | | | 60 ± 4 | a – size of tumor on treatment day 1
b – smallest tumor size from GGTI treatment

FIG. 8

METHODS FOR INDUCING TUMOR REGRESSION, INHIBITING TUMOR GROWTH, AND INDUCING APOPTOSIS IN BREAST TUMORS WITH GERANYLGERANYLTRANSFERASE I INHIBITORS

CLAIM FOR PRIORITY

This is a continuation application claiming the benefit of prior filed International Application Ser. No. PCT/US2010/022498, filed on Jan. 29, 2010 which claims priority to U.S. Provisional Application No. 61/148,244 filed on Jan. 29, 2009, the disclosures of which are hereby incorporated by reference.

STATEMENT OF GOVERNMENT INTEREST

This invention was made with Government support under Grant No. 5U19CA067771 awarded by the National Institute of Health (NIH). The Government has certain rights in this invention.

BACKGROUND

The Ras and Rho family of GTPases are signal transducers that regulate many biological processes including cell cycle progression, cell survival and differentiation. When persistently activated, they promote several oncogenic events including uncontrolled proliferation, resistance to apoptosis, sustained angiogenesis, invasion and metastasis. The ability of the GTPases to mediate these tumorigenic events requires their posttranslational modification with farnesyl and geranylgeranyl lipids. The enzymes responsible for these modifications are farnesyltransferase (FTase) and geranylgeranyltransferase I (GGTase I), and inhibitors of FTase (FTIs) and GGTase I (GGTIs) have been developed as potential anti-cancer drugs. While FTIs are presently undergoing phase II/III clinical trials, GGTIs are in advanced preclinical stages but have not yet entered clinical trials. GGTIs was shown to accumulate tumor cells in the $G_0/G_1$ phase, upregulate the cyclin-dependent kinase (Cdk) inhibitor $p21^{Cip1}$ at the transcriptional level, resulting in inhibition of Cdks and retinoblastoma protein (pRb) hypophosphorylation, and this is a mechanism by which GGTIs block cells in $G_1$. This is consistent with the fact that RhoA downregulates $p21^{Cip1}$ and that inhibition of RhoA geranylgeranylation, which suppresses its function, increases $p21^{Cip1}$ levels. GGTIs also induce tumor cell death, and a mechanism for this is inhibition of Akt activation and suppression of the levels of survivin. However, because ectopic expression of constitutively activated Akt or forced over expression of surviving rescues cancer cells only partially from GGTI effects, other mechanisms may be involved. Rho proteins also decrease the level of another cell cycle regulator, $p27^{Kip1}$ (p27), by enhancing its degradation. Therefore, a mechanism of action for GGTIs is the inhibition of Rho geranylgeranylation and function resulting in increased levels of p27.

In normal cells, p27 inhibits nuclear Cdk activities and is thus considered a tumor suppressor. p27 levels, function and subcellular localization are regulated by phosphorylation on multiple sites. Thus, phosphorylation at Ser10 at the $G_0/G_1$ transition by protein kinase KIS translocates a major portion of nuclear p27 to the cytoplasm, where it is then degraded. The remaining nuclear p27 is regulated by Cdk2-mediated phosphorylation at Thr187 in mid- to late G1 phase, which triggers its degradation by the ubiquitin/proteasome system.

BRIEF DESCRIPTION OF THE DRAWINGS

Reference should be made to the following detailed description, taken in connection with the accompanying drawings, in which:

FIG. 1A illustrates the structures of GGTI-2417, GGTI-2418, GGTI-2431, GGTI-2432, GGTI-2429, and GGTI-2430;

FIG. 1B shows the effects of increasing concentrations of GGTI-2418, GGTI-2432, and GGTI-2430 incubated in the presence of H-Ras-CVLL protein and $^3$H[GGPP] and H-Ras-CVLS and $^3$H[FPP] protein, and their respective inhibition of GGTase I activity (●) and FTase activity (○);

FIG. 1C illustrates results from an in vitro GGTase I competition assay showing the activity against H-Ras-CVLL alone (◇) or in the presence of 10 nM GGTI-2418 (●) and 20 nM GGTI-2418 (▲);

FIG. 1D shows Western blot results of H-Ras transformed NIH-3T3 cells treated in the absence or presence of GGTI compounds for 48 h and processed (U indicates the band for unprenylated H-Ras or Rap1 protein while P indicates the band for fully prenylated H-Ras or Rap1 protein);

FIGS. 2A-2D show that GGTI-2417 induces a concentration-dependent increase of p27 protein levels, $G_0/G_1$ phase accumulation, inhibition of proliferation, and cell death in breast cancer cells (MDA-MB-468 breast cancer cells were treated with compound or vehicle control for 48 h and then processed for various assays);

FIG. 2A illustrates the results of increasing concentrations of GGTI-2417 or 25 μM FTI-2153 on unprenylated Rap1, HDJ-2, and p27 levels;

FIG. 2B illustrates p27 levels in response to GGTI-2417 over time;

FIG. 2C illustrates cell proliferation and cell death by Trypan blue exclusion assays (standard deviations are shown with error bars from three independent experiments);

FIG. 2D shows Western blot assays for MDA-MB-468, MDA-MB-231, SK-Br3, and BT-474 breast cancer cells treated with 50 μM of GGTI-2417 or vehicle; the Western blot assays shown are for Rap1, HDJ-2, and p27 (U and P designate unprocessed and processed forms of the prenylated proteins, respectively);

FIG. 3A shows the effects of p27 levels in response to GGTI-2417 and loss of p27 expression and induction in the presence of p27 siRNA;

FIG. 3B shows the inhibition of proliferation by counting treated cells via Trypan Blue exclusion assay;

FIG. 3C shows the induction of cell death by counting treated cells via Trypan Blue exclusion assay;

FIG. 3D shows that GGTI-2417 increases p27 in wild-type, but not p27 null MEFs, and induces pRb hypophosphorylation in both p27 wild-type and p27 null MEFs.

FIG. 3E shows the inhibition of proliferation by counting treated cells via Trypan Blue exclusion assay;

FIG. 3F shows the induction of cell death by counting treated cells via Trypan Blue exclusion assay (results represent the averages of two independent experiments, each done in triplicates);

FIG. 4A shows results of MDA-MB-468 cells treated with 50 μM GGTI-2417 and processed as for FIGS. 2-3; Western blot analysis of immunoprecipitated p27 with a p27 or phosphotyrosine antibody revealed that p27 amounts increased 11.9-fold, while Tyr phosphorylation increased only 3.5-fold, suggesting a specific downregulation of Tyr74 and/or Tyr88 phosphorylation (upper panel) (there are three Tyr residues in p27, in position 74, 88 and 89, but only Tyr74 and Tyr88 are phosphorylated. GGTI-2417 caused even greater downregulation of Thr187 phosphorylation in p27);

FIG. 4B shows the inhibition of protein synthesis with cycloheximide ((10 μg/ml) 2 h prior to, and during, exposure to) and 50 μM GGTI-2417, which does not prevent the increase in p27 levels;

FIG. 4C shows representative immunofluorescence images showing that a 48 h exposure of MDA-MB-468 cells to GGTI-2417 upregulates nuclear p27, where it can function as a Cdk inhibitor;

FIG. 4D shows quantitative analysis of the relative cellular amounts of p27 in the nucleus and cytoplasm (595 vehicle-treated cells in 6 fields and 447 GGTI-2417-treated cells in 11 fields were analyzed. The plotted values were computed with the formula number of pixels×intensity/number of cells. The value for vehicle-treated cells was set to 100%. The columns represent the mean±standard error of the mean (S.E.M.));

FIG. 5A shows results of nude mice implanted with MDA-MB-231 breast cancer tumors in the mammary fat pads were injected i.p. daily with either vehicle (♦), 100 mg/kg GGTI-2418 daily (□) or 200 mg/kg GGTI-2418 every $3^{rd}$ day (Δ);

FIGS. 5B-C show the effects of GGTI-2418 treatment on mammary tumor progression in ErbB2 transgenic mice;

FIG. 5D shows the effects of GGTI-2418 on p27 in vivo (tumor biopsies were obtained from mice before and after vehicle or GGTI-2418 treatment and prepared for Western blot analyses of select proteins; GGTI-2418 accumulates unprenylated Rap1 and prevents the activation of Akt. GGTI-2418 also upregulates p27 levels in vivo. The numbers above the Western blot indicate the -fold change in post-treatment samples, as determined by densitometric analysis. The change was 0.63±0.19 fold in vehicle-treated and 2.68±0.63 fold in GGTI-2418-treated mice (p=0.03));

FIG. 6 is a table showing GGTI-2417 induces G0/G1 phase accumulation;

FIG. 7 is a table showing effects of 50 μM GGTI-2417 on proliferation, cell death, and cell cycle distribution; and FIG. 8 is a table showing GGTI-2418 causes breast tumor regression in vivo.

DETAILED DESCRIPTION

Figure 1A:
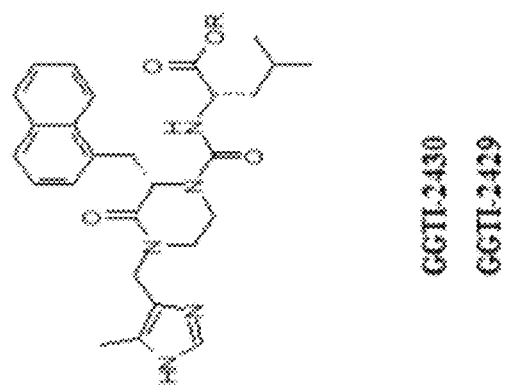
FIGS. 1A-1D illustrate that GGTI-2418 and its prodrug GGTI-2417 are potent and selective inhibitor of GGTase I activity in vitro and in whole cells.
Figure 1A:
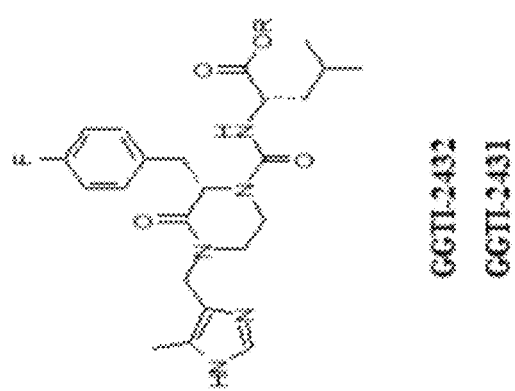
Figure 1A:
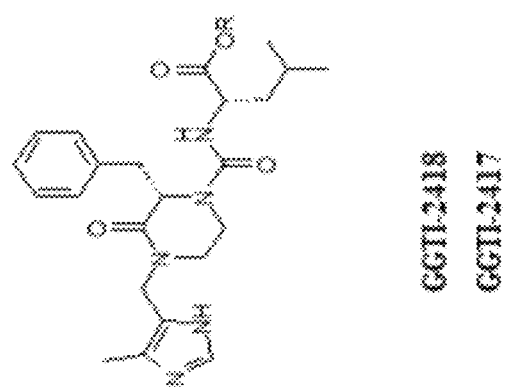

In the following detailed description, reference is made to the accompanying drawings, which form a part hereof. It is to be understood that other aspects may be utilized and structural changes may be made without departing from the scope of the claims.

A brief discussion of exemplary materials and methods follows. In vitro FTase and GGTase I activity assays were performed. GGTase I and FTase activities from 60,000×g supernatants of human Burkitt's lymphoma (Daudi) cells (American Type Culture Collection (ATCC), Rockville, Md.) were assayed as described previously. Lerner, E. C., et al., Ras CAAX peptidomimetic FTI-277 selectively blocks oncogenic Ras signaling by inducing cytoplasmic accumulation of inactive Ras-Raf complexes, J Biol Chem 270: 26802-6 (1995) Inhibition and kinetics studies were performed by determining the ability of peptidomimetics or CVLL peptide to inhibit the transfer of [$^3$H]geranylgeranyl and [$^3$H]farnesyl from [$^3$H]geranylgeranylpyrophosphate ([$^3$H]GGPP (Perkin Elmer, Wellesley, Mass.) and [$^3$H]farnesylpyrophosphate ([$^3$H]FPP, Amersham Biosciences, Piscataway, N.J.) to recombinant H-Ras-CVLL and H-Ras-CVLS, respectively.

Cell Culture.

Human MDA-MB-468 and MDA-MB-231 breast cancer cells and murine NIH 3T3 cells were obtained from the ATCC and cultured in DMEM medium. Human SK-Br3 and BT-474 breast cancer cells (ATCC) were cultured in McCoy's 5a medium and Hybri-Care medium, respectively. Mouse embryonic fibroblast (MEF) cells from p27 wild-type and p27 null mice were grown in DMEM. All media were supplemented with 10% fetal calf serum, 10 units/ml penicillin, and 10 μg/ml streptomycin. Subconfluent cells were treated with different concentrations of GGTI, FTI or DMSO vehicle for specific time periods. After treatment, cells were harvested by trypsinization.

siRNA-Mediated Knockdown of p27 in MDA-MB-468 Cells.

Pre-designed siRNA to p27 (Cat #118714) and the negative control (Cat #4611) were purchased from Ambion (Austin, Tex.). Twenty-four hours before transfection, MDA-MB-468 cells were plated onto twelve-well plates in fresh DMEM medium containing 10% FBS and no antibiotics. Transient transfection of siRNA was carried out using Oligofectamine reagent (Invitrogen, Carlsbad, Calif.), following the manufacturer's instructions. In brief, 5 nM of p27 siRNA or control siRNA were mixed with Opti-MEM medium (Invitrogen) in such a way so that the total volume went to 90 μl, and then complexed with a mixture of 2 μl of Oligofectamine and 8 μl Opti-MEM; the total volume of RNA:Oligofectamine complex was 100 μl. The RNA:Oligofectamine complex was then incubated for 20 min at room temperature before adding to the cells. Before transfection, the old medium was discarded, cells were washed once with fresh Opti-MEM and 400 μl of fresh Opti-MEM placed into each well before adding the RNA:Oligofectamine complex to each well. The final diluted volume on each well was 500 μl. After 8 h, 500 μl DMEM containing 30% FBS was added to each well and cells were further incubated for 40 h.

Immunoprecipitation of p27 Protein.

MDA-MB-468 cells were lysed using CelLytic™ M Cell Lysis Reagent (Sigma-Aldrich, St. Louis, Mo.) containing protease inhibitor cocktail, 2 mM phenylmethylsulfonylfluoride (PMSF), 2 mM Na$_3$VO$_4$, and 6.4 mg/ml p-nitrophenylphosphate (Sigma-Aldrich). Lysates were incubated overnight with p27 antibody (BD Biosciences, San Jose, Calif.) at 4° C. while rocking; after incubation protein A anti-IgG agarose beads were added and incubated for 2 h at 4° C., then washed four times with an excess of lysis buffer. Samples were then boiled at 100° C. for 10 min in 2×SDS-sample buffer and analyzed by Western blotting as described below.

Western Blot Analysis.

To prepare whole cell lysates, cells were trypsinized, washed with phosphate buffered saline (PBS) twice, and lysed in 30 mM Hepes, pH 7.5, 10 mM NaCl, 5 mM $MgCl_2$, 25 mM NaF, 1 mM EGTA, 1% Triton-X-100, 10% glycerol, protease inhibitor cocktail, 2 mM PMSF, 2 mM $Na_3VO_4$, and 6.4 mg/ml p-nitrophenylphosphate. Lysates were cleared by centrifugation at 12,000×g for 15 min, and the supernatants were collected as whole cell extracts. The protein concentration was determined by the Bradford assay. Proteins were separated by SDS-PAGE and transferred to nitrocellulose membranes, which were then blotted with antibodies specific for whole Rap1 or unprenylated Rap1, Ras, the C-terminal region of pRb, Akt (Santa Cruz Biotechnology, Santa Cruz, Calif.), phospho-Akt(S473) (Cell Signaling, Danvers, Mass.), p27 (BD Biosciences, San Jose, Calif.), phospho-p27(T187) (Invitrogen, Carlsbad, Calif.), HDJ-2 (Lab Vision Corporation, Fremont, Calif.), phosphotyrosine (Millipore, Billerica, Mass.), and β-actin (Sigma-Aldrich, St. Louis, Mo.). Select bands were quantified using AlphaEaseFC densitometry software (AlphaInnotech, San Leandro, Calif.).

Trypan Blue Exclusion Assay.

Adherent cells were harvested by trypsinization and diluted with 0.4% Trypan Blue dye and counted on a hemacytometer. Cells excluding the dye were scored as live cells, whereas cells absorbing the dye were scored as dead cells. Cell proliferation was determined by dividing the number of live cells in the treated sample by the number of live cells in the control, and the degree of cell death was expressed as percentage of dead cells of the total cell number.

Cell Cycle Analysis.

Cell cycle analysis based on DNA content was performed as described previously. Liang, J., et al., PKB/Akt phosphorylates p27, impairs nuclear import of p27 and opposes p27-mediated G1 arrest, Nat Med 8:1153-60 (2002). At each time point, cells were harvested, counted, and washed twice with PBS. Cells ($2-3 \times 10^6$) were suspended in 0.5 ml PBS, fixed in 5 ml of 70% ethanol overnight at −20° C., centrifuged, re-suspended again in 1 ml of propidium iodide staining solution (50 μg/ml propidium iodide, 100 units/ml RNase A and 1 mg/ml of glucose in PBS), and incubated at room temperature for 30 min. The cells were then analyzed for cell cycle distribution using FACScan (BD Biosciences) and ModFit LT cell cycle analysis software (Verity Software, Topsham, Me.).

Immunofluorescence.

MDA-MB-468 cells were plated on a glass coverslip and treated with 50 μM GGTI-2417 or DMSO as a control for 48 h. Medium was aspirated and the cells were washed twice with ice-cold sterile DPBS solution (Invitrogen, Carlsbad, Calif.), fixed with 4% paraformaldehyde at room temperature for 15 min, and then treated with 1% Nonidet P-40 for 30 min at room temperature. After blocking with 5% bovine serum albumin for 30 min at room temperature, cells were incubated with anti-p27 antibody (1:500) at room temperature for 1 h. After washing three times with DPBS solution, cells were incubated with FITC-conjugated secondary antibody (1:1000) for 1 h at room temperature. Cells were then washed three times with sterile DPBS solution, mounted using Vectashield mounting reagent (Vector Laboratories, Inc., Burlingame, Calif.) containing 4',6'-diamidino-2-phenylindole (DAPI) for nuclear visualization, and analyzed using a Zeiss Axiovert Z-1 Imager microscope (Carl Zeiss, Oberkochen, Germany) at 525 nM (FITC) and 420 nM (DAPI). Images were analyzed using ImagePro Plus 6.2 (Media Cybernetics, Bethesda, Md.).

Anti-Tumor Activity in the Nude Mouse Tumor Xenograft Model.

Nude mice (nu/nu, Charles River, Wilmington, Mass.) were maintained in accordance with the Institutional Animal Care and Use Committee (IACUC) procedures and guidelines. MDA-MB-231 cells were harvested via trypsinization, pelleted at 805×g for 5 min, and re-suspended in a 50:50 mixture of sterile PBS and Matrigel (BD Biosciences) at $10 \times 10^6$ cells per 100 μl. A volume of 100 μl (~$10 \times 10^6$ cells) was injected orthotopically into the upper mammary fat pads of nude mice. The tumor xenografts were monitored by electronic caliper measurements and tumor volume (V) was calculated using the formula $V=W^2L/2$, where width (W) is the largest diameter and length (L) is the smallest diameter. When the tumors reached ~100 $mm^3$, the animals were randomized and injected intraperiteoneally daily with vehicle (70% DMSO), or 100 mg/kg GGTI-2417 or GGTI-2418, or every third day with GGTI-2418 (200 mg/kg. Tumors were measured every third day for 12-18 days.

Anti-Tumor Activity in the ErbB2 Transgenic Mouse Model.

A breeding pair of homozygous FVB/N-Tg (MMTVneu) 202Mul/J mice (JAX #002376, Bar Harbor, Me.) was used to generate a transgenic colony in accordance to IACUC protocols and procedures. Phenotypically, these mice overexpress the receptor tyrosine kinase ErbB2 driven by the MMTV promoter, which results in tumor formation at ~200 days of age. Once tumors reached sizes above 800 $mm^3$, osmotic mini-pumps (Alzet, Cupertino, Calif.) were loaded with either vehicle (80% PEG300; 20% DMSO) or GGTI-2418 (100 mg/kg daily) and implanted subcutaneously under the dorsal surface of the mouse, between the shoulder blades. Vehicle or GGTI-2418 was constantly delivered for 14 days, during which tumor volumes were measured and calculated as described above. Tumor biopsies were snap frozen in liquid $N_2$ and stored at −80° C. until further processed. Weighted tumor samples were mixed with the appropriate amount of T-PER® Tissue Protein Extraction Reagent (Pierce, Rockford, Ill.) containing protease inhibitor cocktail, 2 mM PMSF, 2 mM $Na_3VO_4$, and 6.4 mg/ml p-nitrophenylphosphate and homogenized with the PCR Tissue Homogenizing Kit (Fisher Scientific). The homogenate was centrifuged at 13,000×g for 30 min at 4° C. and the supernatant was subjected to Western blotting with the indicated antibodies.

Figure 1B:
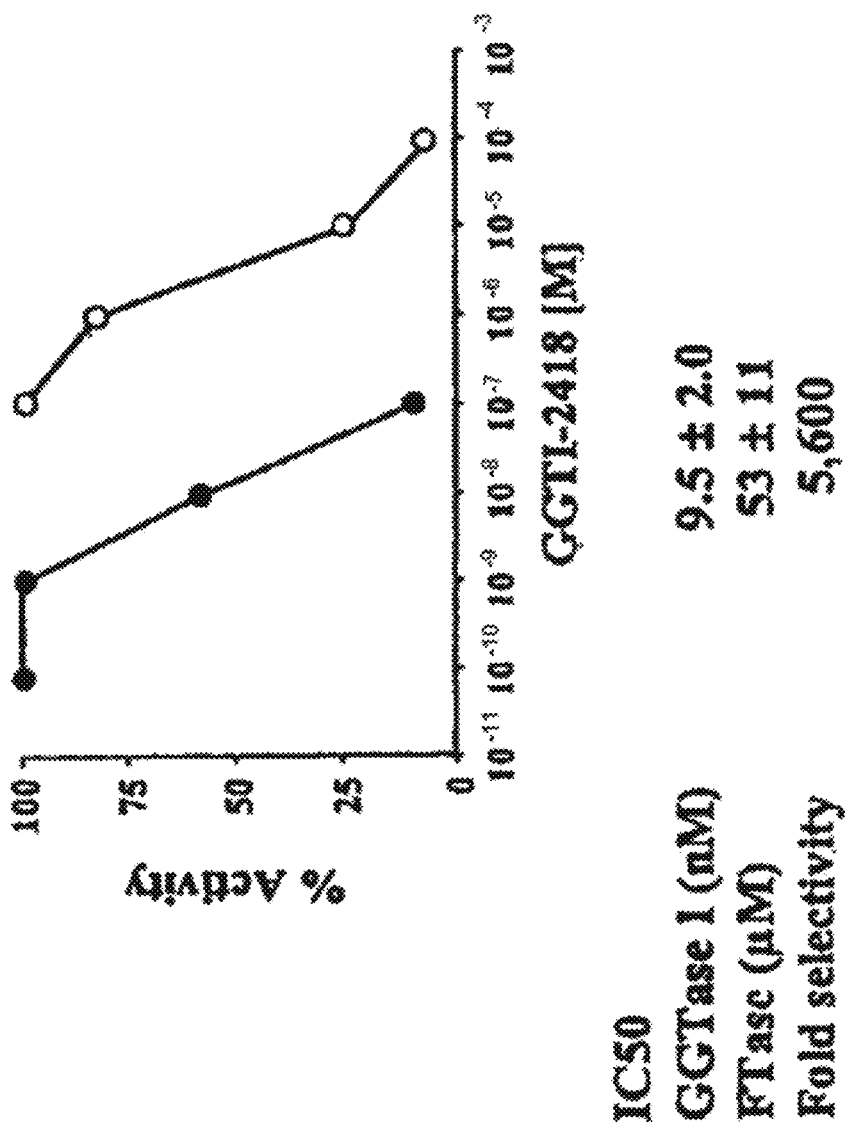
Figure 1C:
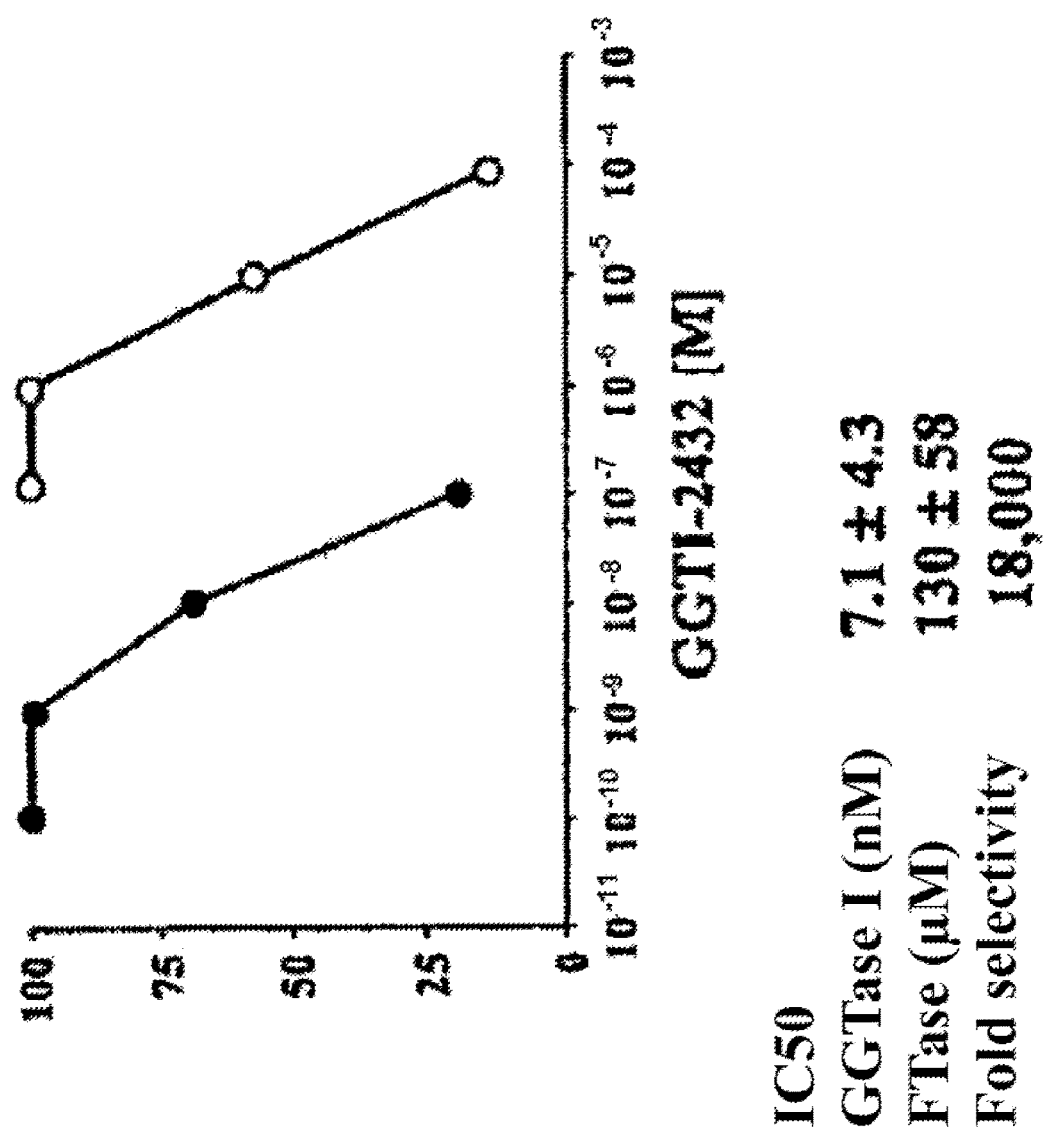

GGTI-2418 is a highly potent, competitive and selective inhibitor of GGTase I in vitro. Protein prenyltransferases such as GGTase I and FTase modify the carboxyl terminal cysteines of proteins terminating with CAAX tetrapeptide sequences (SEQ ID NO: 2) where C=cysteine, A=aliphatic residues and X=any amino acid. GGTase I prefers proteins where X is a leucine, whereas FTase prefers methionine or serine at the X position. Cys-A-A-Leu peptidomimetics were designed where cysteine was replaced with methyl imidazole and the dipeptide "A-A" was replaced by 3-arylpiperazin-2-one derivatives (FIG. 1A). The synthesis of these peptidomimetics has been described elsewhere. This description includes the characterization of the biochemical activities of some of these peptidomimetics and determine the mechanism by which they induce cell death in breast cancer. FIGS. 1A and 1B show the structures and activities of the most potent and selective of these compounds. In vitro, GGTI-2418 inhibited GGTase I and FTase activities with IC$_{50}$ values of 9.5±2.0 nM and 53±11 μM, respectively, a 5.600-fold selectivity towards inhibition of GGTase I versus FTase. Two other compounds substituting either p-fluorphenyl (GGTI-2432) or naphthyl (GGTI-2430) groups for the phenyl group of GGTI-2418 showed similarly potency against GGTase I in vitro (IC$_{50}$ values of 7.1±4.3 nM and 14±6.4 nM, respectively). The FTase inhibition activities of these two compounds indicate that GGTI-2432 and GGTI-2430 were 18,000- and 340-fold more selective for GGTase I over FTase, respectively. The K$_m$ and V$_{max}$ values obtained for H-Ras-CVLL were 2.8 μM and 0.07 pmol/min, respectively. GGTI-2418 demonstrated competitive inhibition of GGTase I against the H-Ras-CVLL protein with a K$_i$ value of 4.4±1.6 nM (FIG. 1C).

GGTI-2417 selectively inhibits protein geranylgeranylation in H-Ras transformed NIH 3T3 cells.

Figure 1D:
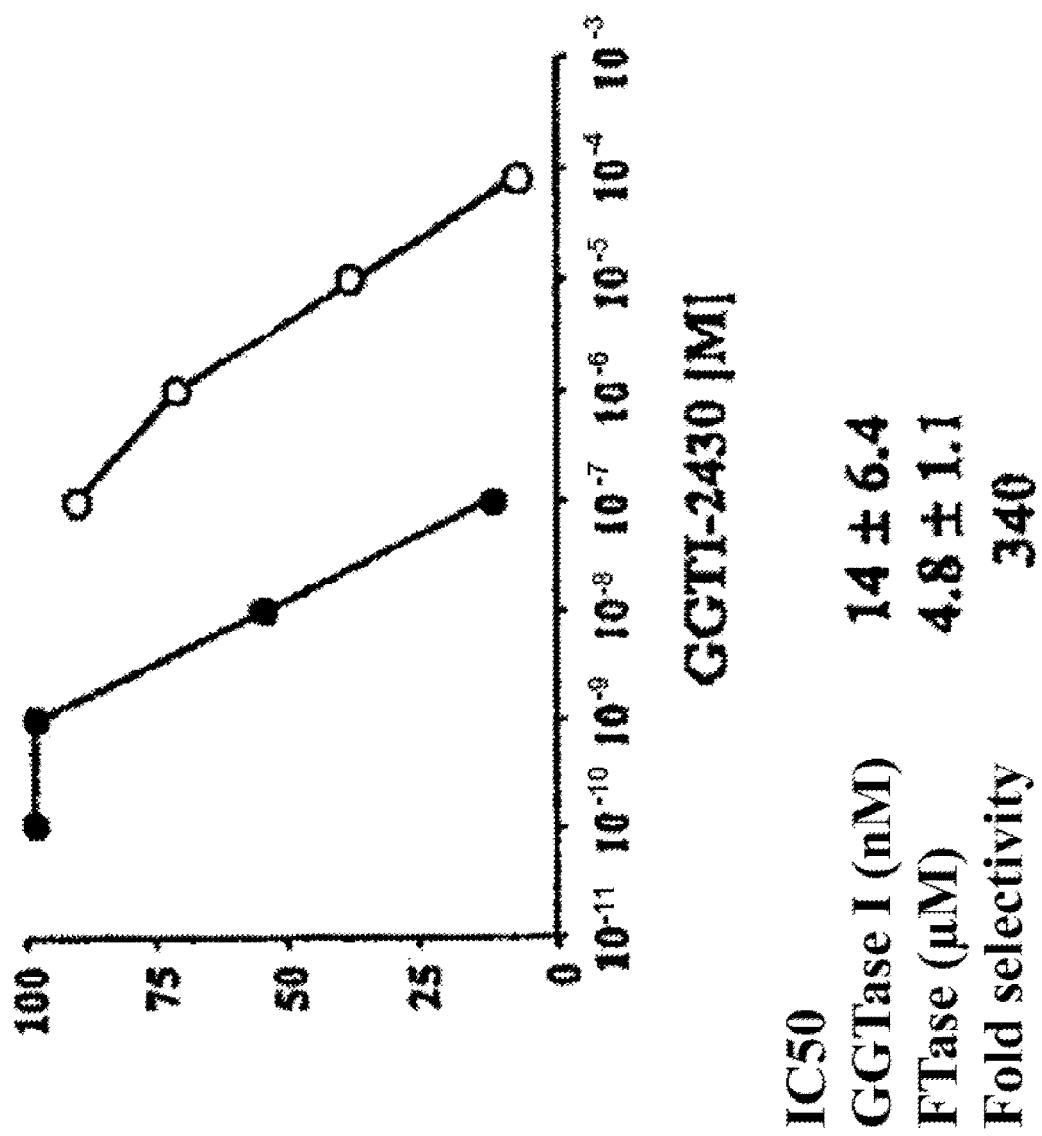

A methyl ester pro-drug strategy (FIG. 1A) was employed, which allows the compounds to more easily cross the plasma membrane, thus facilitating delivery of these drugs to cells. NIH 3T3 cells stably transformed with GTP-locked H-Ras (61 L) (H-Ras/3T3) were treated with increasing concentrations of GGTIs. FIG. 1D shows that GGTI-2417 exhibited the most potent inhibitory activity against Rap1 geranylgeranylation, with an IC$_{50}$ value of 400±100 nM, followed by GGTI-2429 and GGTI-2431 with IC$_{50}$ values of 600 nM and 700 nM, respectively. Half-maximal inhibition of H-Ras farnesylation required GGTI concentrations of >50 μM. Each compound thus showed high selectivity for inhibition of cellular GGTase I compared to FTase, the most selective being GGTI-2417, with >125-fold selectivity (FIG. 1D). Therefore, GGTI-2417 and GGTI-2418 were used as the most potent and selective inhibitors for the remainder of the study.

GGTI-2417 increases p27 protein levels, induces accumulation in the G$_0$/G$_1$ phase and cell death in breast cancer cells.

Figure 2A:
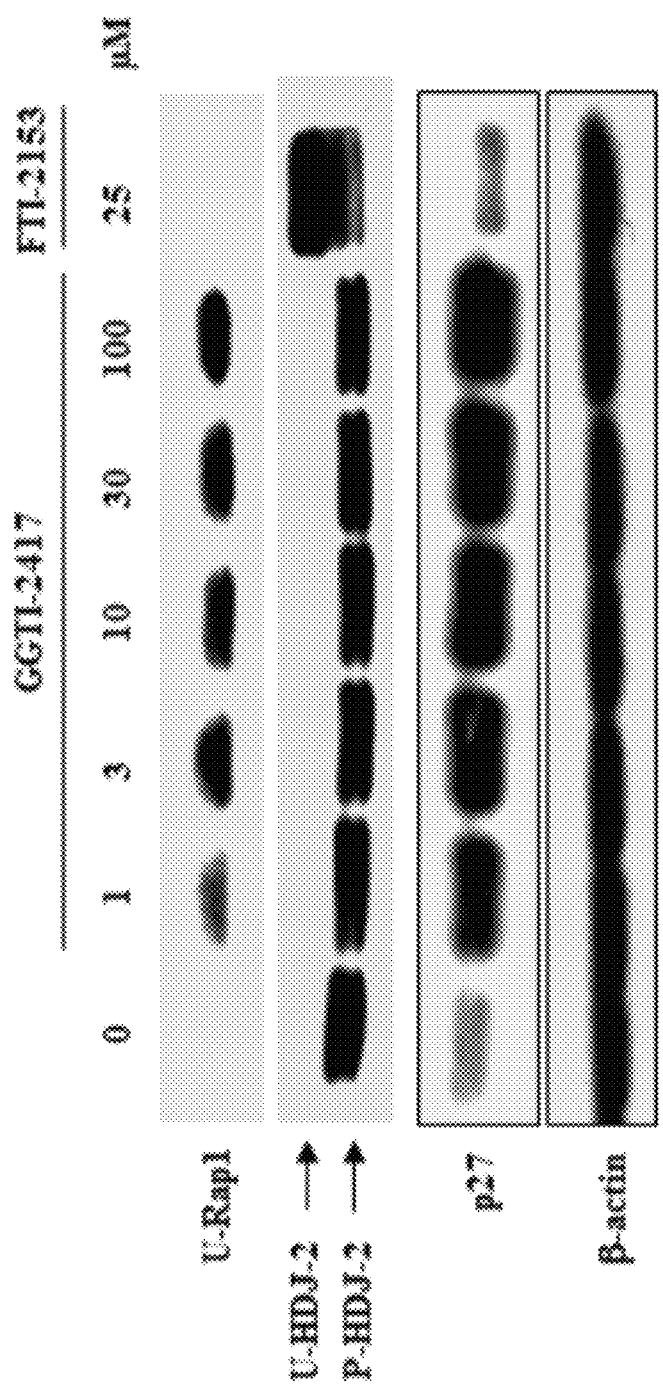

Low levels of nuclear p27 are associated with poor prognosis for various cancers, especially breast cancer. Because RhoA is geranylgeranylated and downregulates nuclear p27, it was determined whether inhibition of protein geranylgeranylation affects p27 levels. MDA-MB-468 cells were treated for 48 h with different concentrations of GGTI-2417, vehicle control or 25 μM FTI-2153, a highly selective FTase but not a GGTase I inhibitor. GGTI-2417 inhibited the geranylgeranylation of Rap1, but not the farnesylation of HDJ-2, an exclusively farnesylated protein, in a dose-dependent manner (FIG. 2A). GGTI-2417 increased p27 protein levels in a time-dependent manner starting after 12 h exposure to GGTI-2417 (FIG. 2B). However, as expected, FTI-2153 completely inhibited HDJ-2 processing, did not inhibit Rap1 geranylgeranylation, and failed to increase p27 (FIG. 2A, lane 7). These results suggest that the increase of p27 correlates with inhibition of protein geranylgeranylation but not protein farnesylation.

Figure 2C:
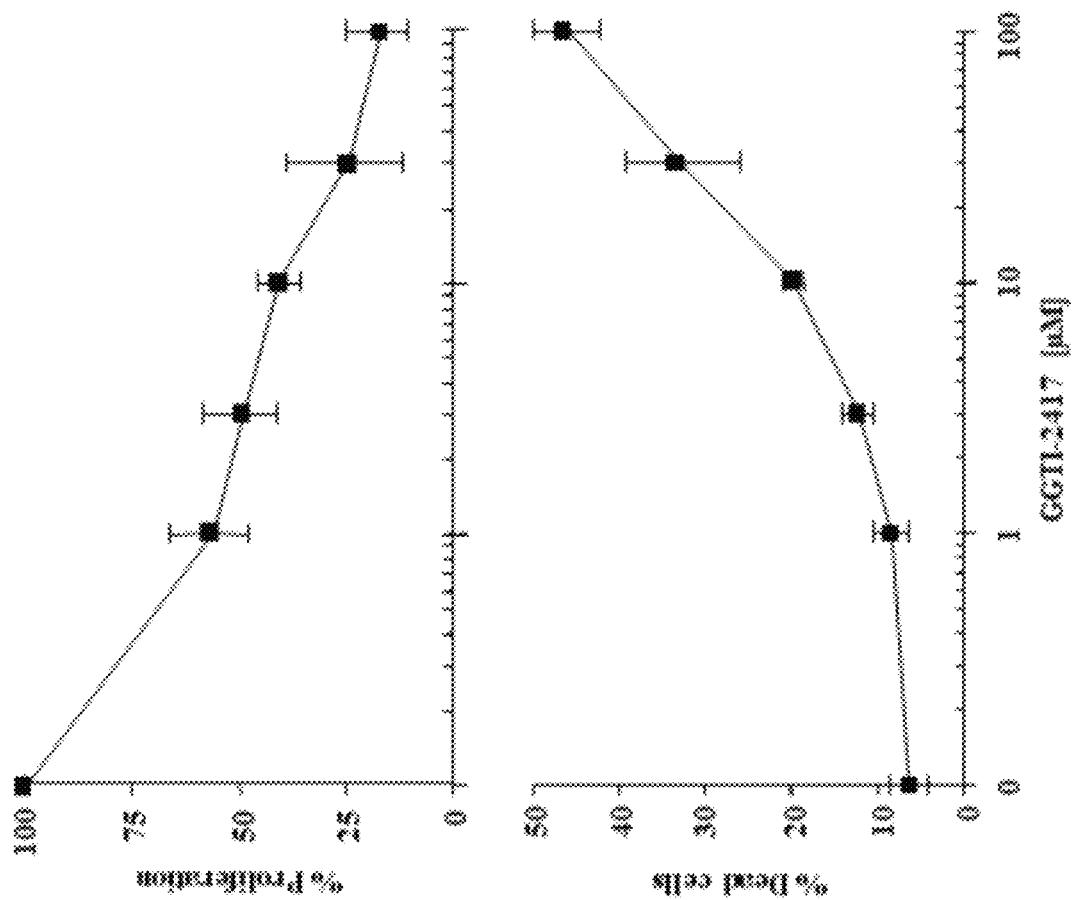

GGTI-2417 inhibited cell proliferation in a dose-dependent manner compared to control cells, with an IC$_{50}$ value of approximately 4 μM (FIG. 2C, upper panel). These results suggest that inhibition of proliferation induced by GGTI-2417 correlates closely with the concentration-dependent increase of p27 protein levels as seen in FIG. 2A. This was most likely due to accumulation in the G$_0$/G$_1$ phase of the cell cycle: 50 μM GGTI-2417 increased the fraction of cells in G$_0$/G$_1$ from 51 to 78% (FIG. 6). Furthermore, Trypan Blue-positive (dead) cells increased in a concentration-dependent manner following GGTI-2417 treatment (FIG. 2C, lower panel).

Figure 2D:
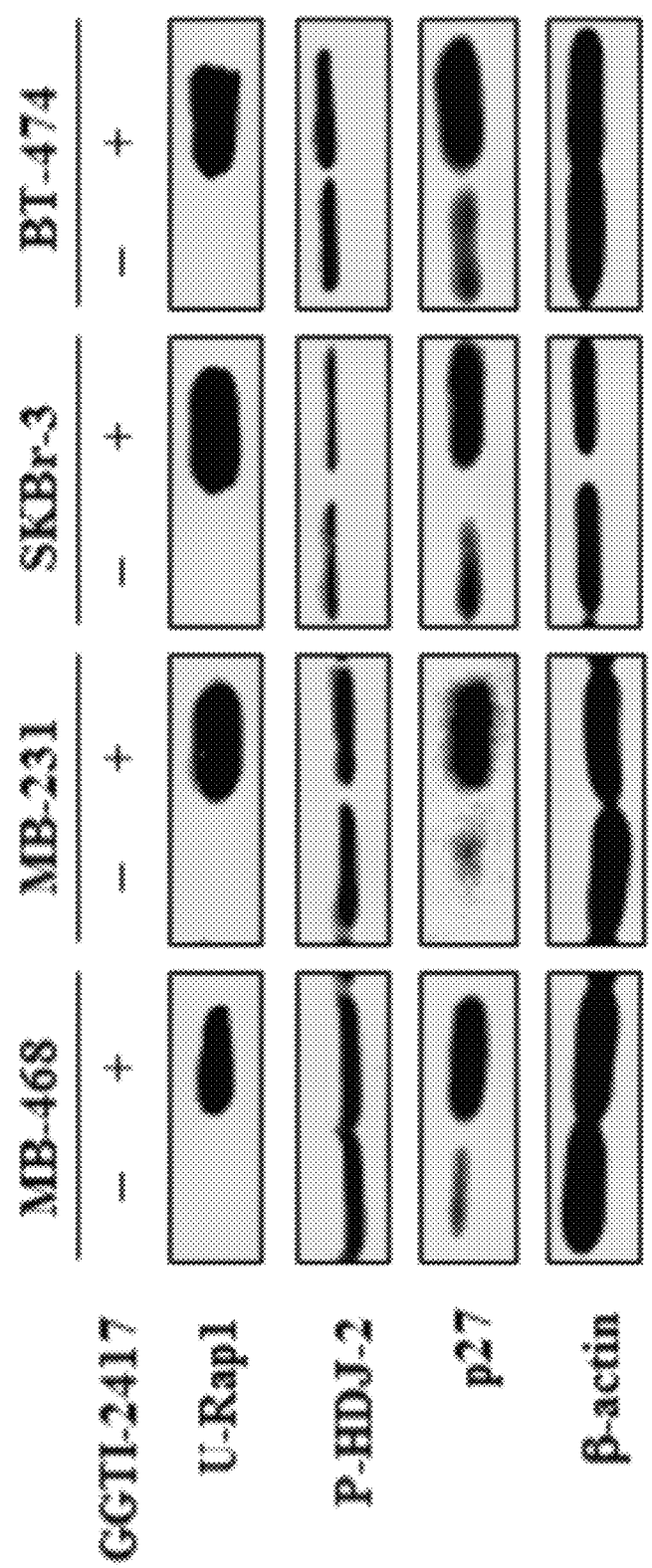

To examine whether GGTI-2417 has similar effects in other human breast cancer cell lines, MDA-MB-231, SK-Br3 and BT-474 breast cancer cells were also exposed to 50 μM GGTI-2417. Similar to the MDA-MB-468 cells, which were included as a control, this treatment inhibited the processing of Rap1A, but not HDJ-2, induced p27 protein levels (FIG. 2D), inhibited cell proliferation, increased the fraction of cells in the G$_0$/G$_1$ phase as well as the percentage of cell death in all three cell lines (FIG. 7).

Figure 3A:
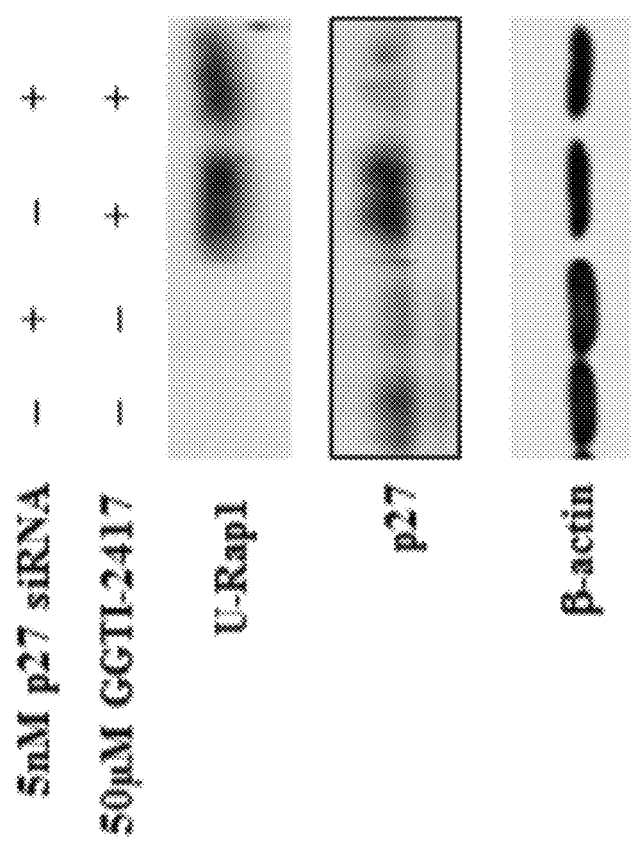
FIGS. 3A-C show that p27 is required for the induction of cell death by GGTI-2417 (siRNA-mediated silencing of p27.MDA-MB-468 cells treated with 50 μM GGTI-2417, 1 μM taxol or vehicle (DMSO) in the absence or presence of p27 siRNA)
Figure 3B:
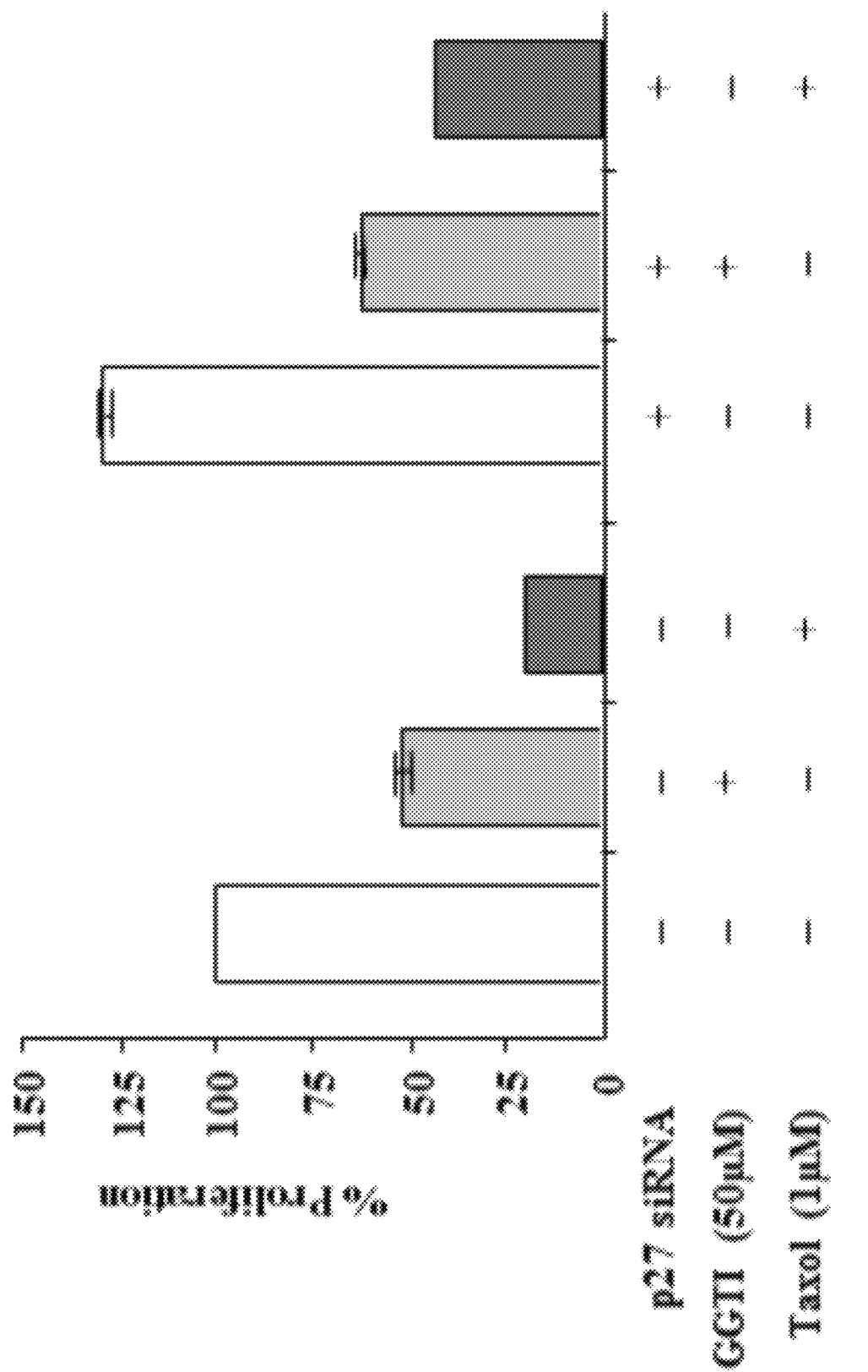
Figure 3C:
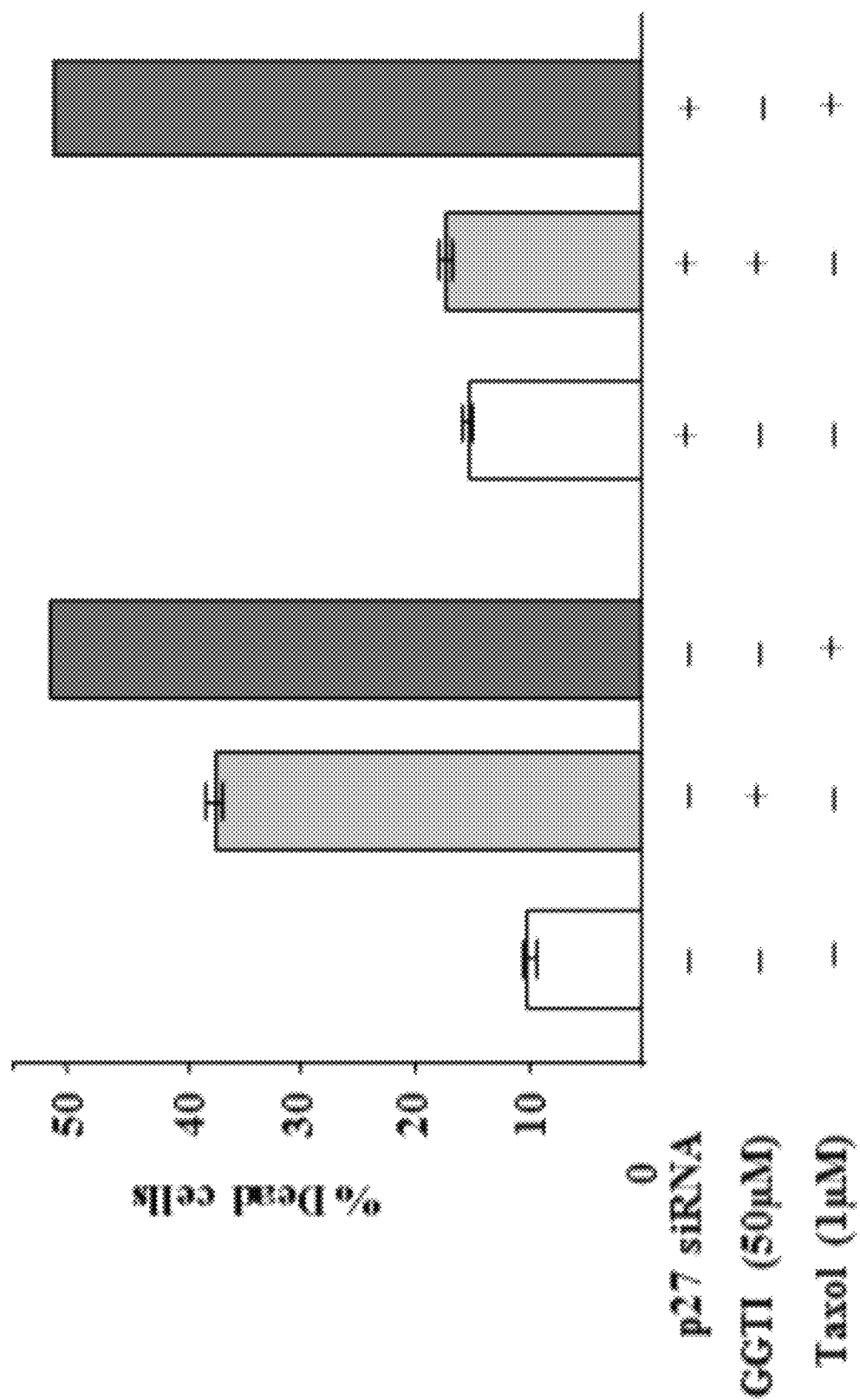

Knockdown of p27 protein levels by siRNA results in resistance to GGTI-2417-induced cell death in MDA-MB-468 cells. To determine whether the inhibition of proliferation and/or induction of tumor cell death requires p27, p27 was knocked down using an siRNA approach. FIG. 3A shows that in the presence of p27 siRNA, the ability of GGTI-2417 to induce p27 expression was blocked. While co-treatment with p27 siRNA did not significantly affect the ability of GGTI-2417 to inhibit proliferation in MDA-MB-468 cells (FIG. 3B), it rescued the cells from GGTI-2417-induced cell death (FIG. 3C). In the absence of p27 siRNA, GGTI-2417 increased tumor cell death from 10.3 to 37.2%. In contrast, in the presence of 5 nM p27 siRNA, GGTI-2417 was unable to induce tumor cell death. However, these p27-deficient cells could still die in response to other known apoptotic stimuli, e.g. taxol (FIG. 3C), suggesting that cell death in response to GGTI-2417, and not cell death per se, requires p27. Taken together, these results indicate a pivotal role for p27 in the ability of GGTI-2417 to induce breast tumor cell death.

Figure 3D:
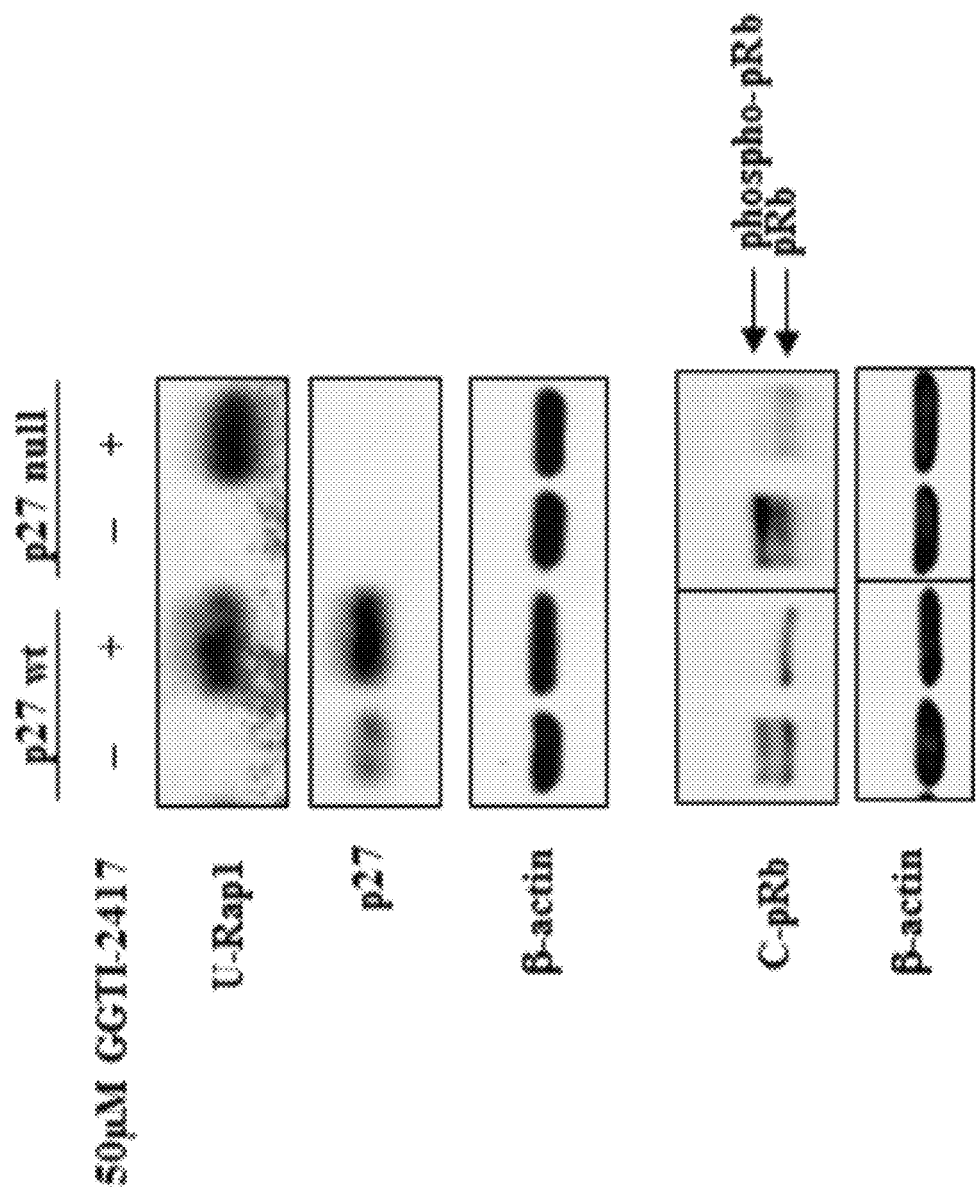
FIGS. 3D-F show that some amount of p27 is required for the induction of cell death by GGTI-2417 (mouse embryonic fibroblasts (MEFs)) lacking p27 expression are unable to die in response to GGTI-2417); p27 wild-type and p27 null MEFs were treated with 50 μM GGTI-2417 for 72 h and processed for further assays.

GGTI-2417 does not induce cell death in MEF cells lacking p27. To further study the role for p27 in the induction of cell death by GGTI-2417, wild-type MEFs and MEFs lacking p27 (p27 null) were exposed to 50 μM of GGTI-2417. In wild-type MEFs, as in human breast cancer cells, GGTI-2417 inhibited Rap1A geranylgeranylation and increased the levels of p27 (FIG. 3D). As expected, in p27 null MEFs, there was no basal p27 expression. GGTI-2417 also induced pRb hypophosphorylation in p27 wild-type as well as p27 null MEFs, suggesting that the ability of GGTI-2417 to arrest cells in G$_1$ (see FIG. 6) does not depend on p27 (FIG. 3D, lower panel).

Figure 3E:
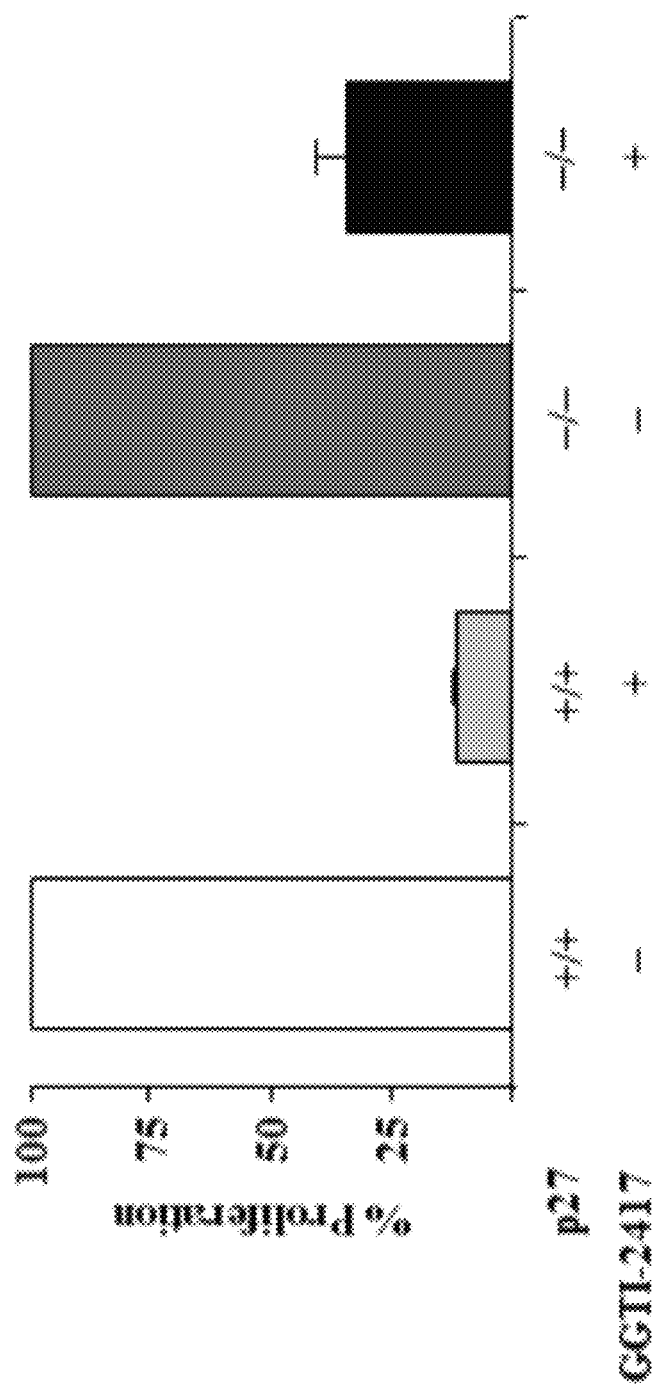
Figure 3F:
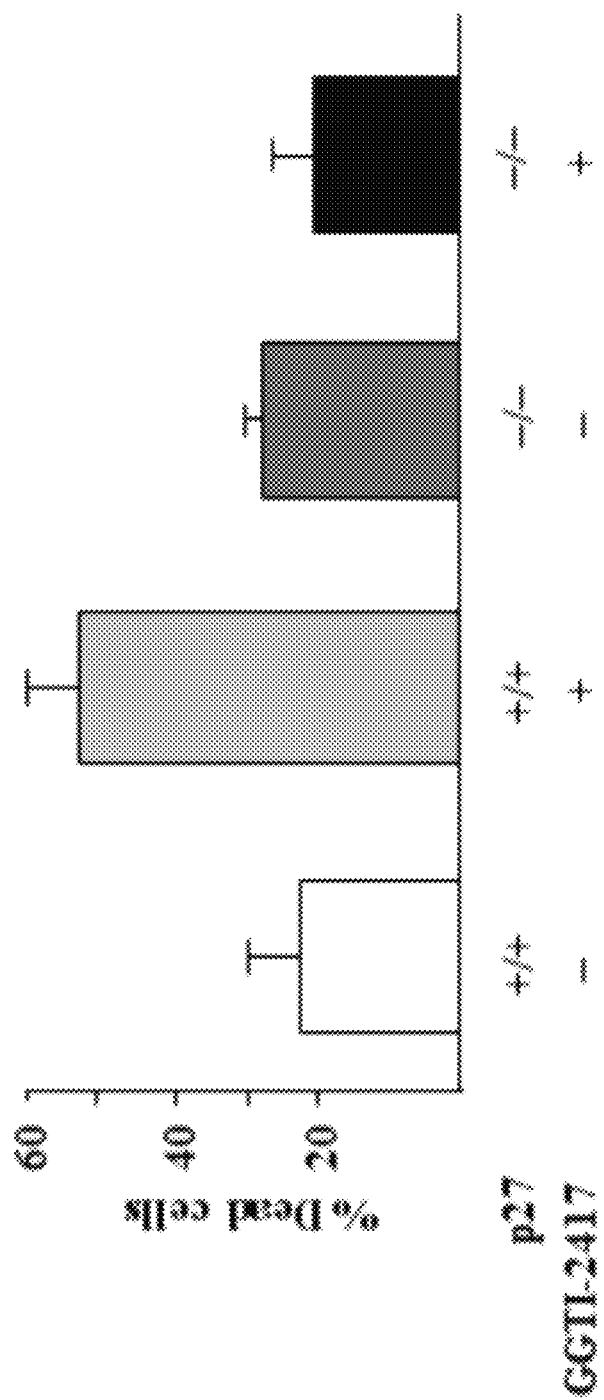

GGTI-2417 treatment was associated with potent inhibition of proliferation in p27 wt MEFs (89.0±3.1%) and MEFs lacking p27 (61.6±8.1%) (FIG. 3E), which is consistent with the pRb phosphorylation state reported above. In p27 wt MEFs, GGTI-2417 also strongly induced cell death from 22.4±7.2% in vehicle-treated cells to 53.4±7.0% (FIG. 3F). p27 null cells showed slightly higher basal levels of cell death (27.5±2.1%); however, treatment with GGTI-2417 did not increase the number of dead cells (FIG. 3F).

Figure 4A:
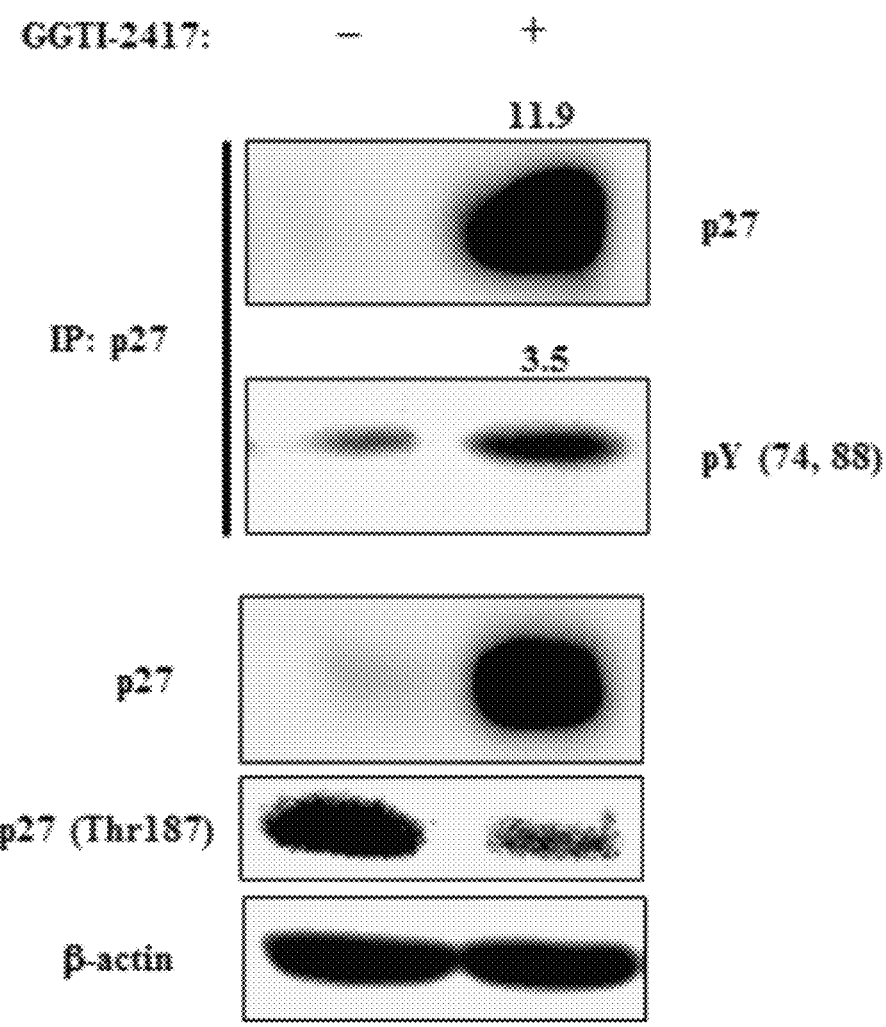
FIGS. 4A-D show that GGTI-2417 inhibits phosphorylation events that are required for subsequent p27 degradation and accumulates nuclear p27.
Figure 4B:
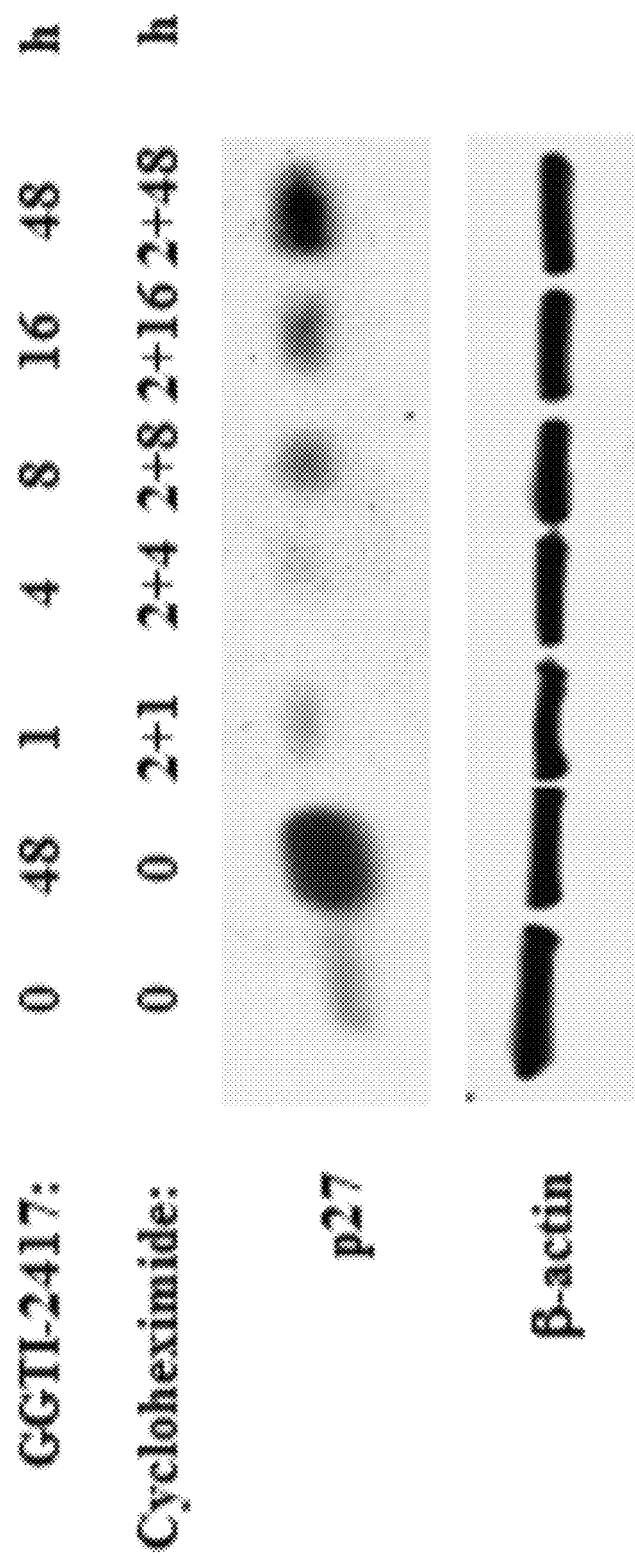
Figure 4C:
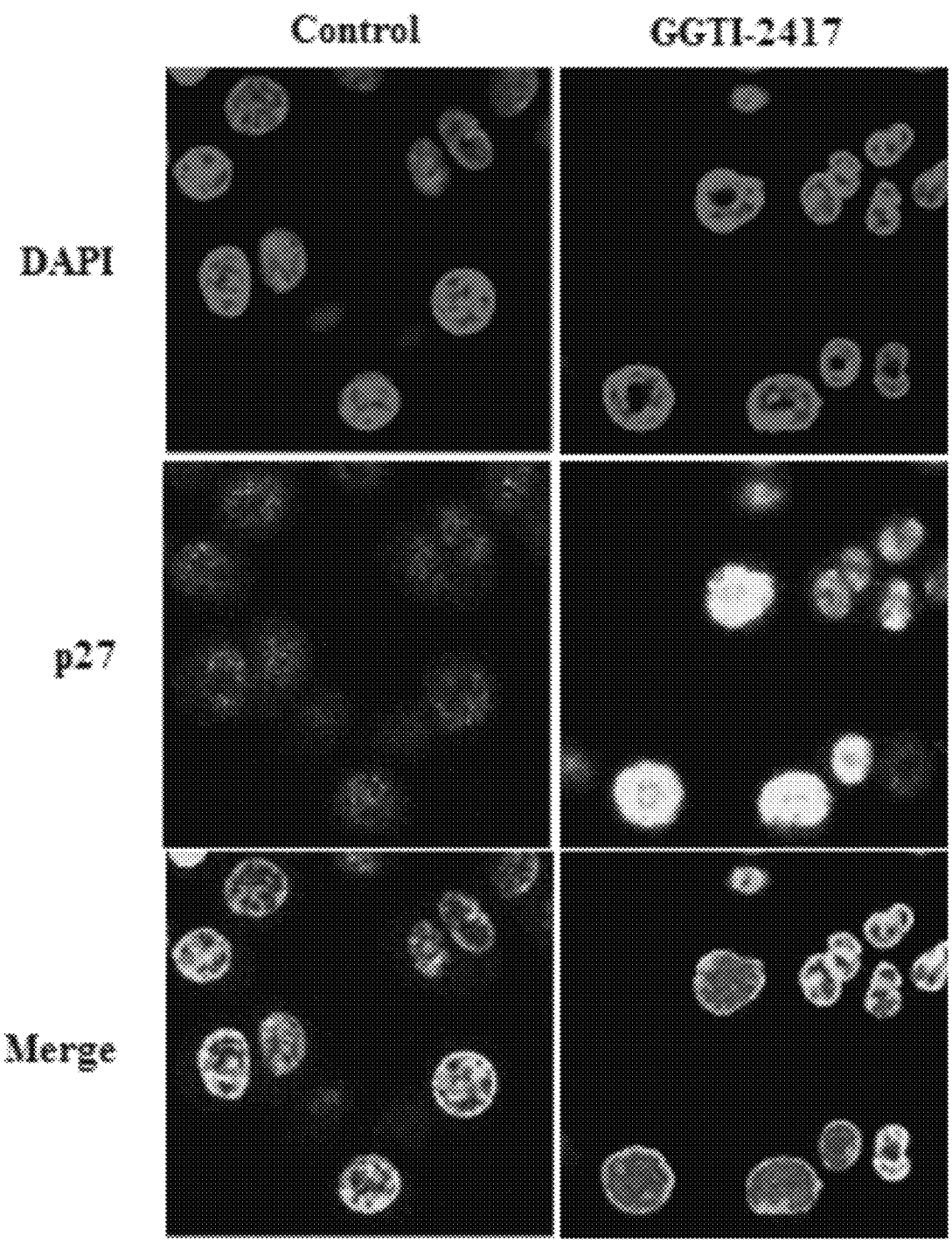
Figure 4D:
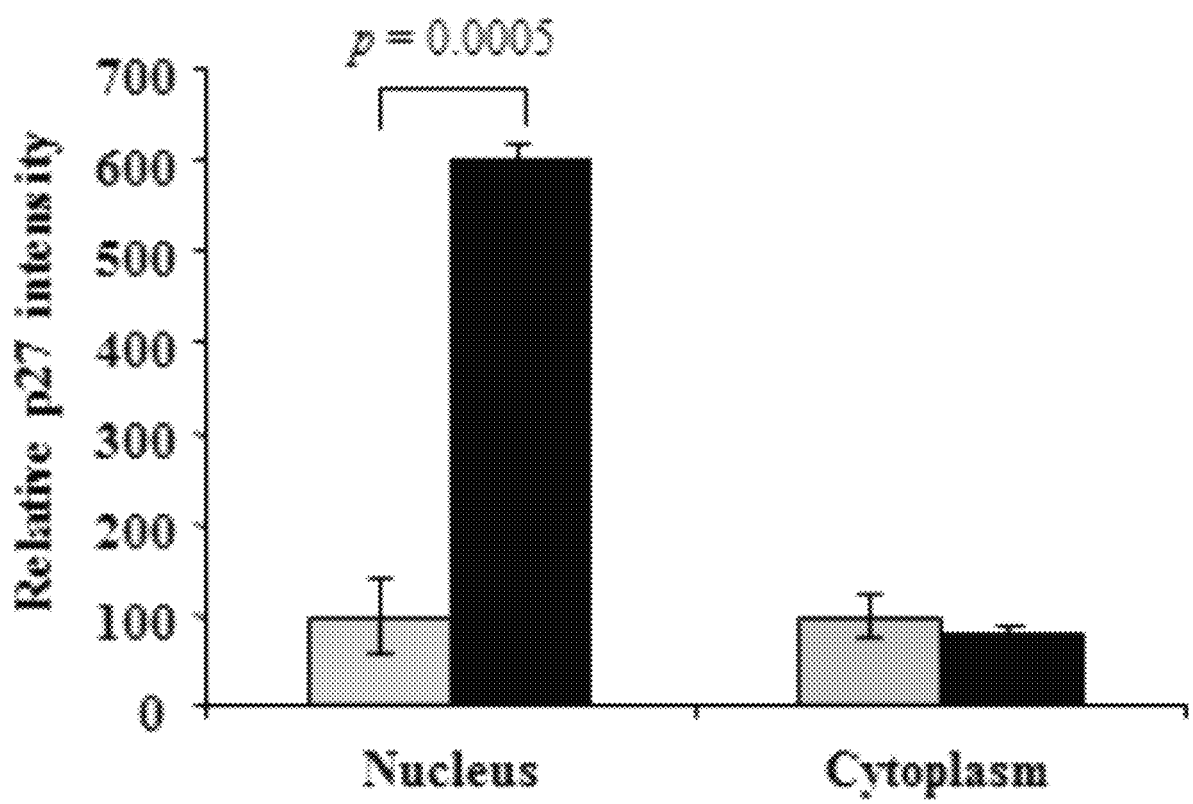

GGTI-2417 prevents the degradation of nuclear p27. Since the RhoA-dependent downregulation of p27 appears to be mediated by Cdk2-mediated phosphorylation, which in turn depends on prior phosphorylation in two Tyr residues, next it was determined whether GGTI-2417-induced increase in p27 levels were associated with altered p27 phosphorylation. Indeed, FIG. 4A shows that GGTI-2417 inhibited the phosphorylation of p27 at Tyr74 and/or Tyr88 and, even more dramatically, at Thr187. Accordingly, cycloheximide did not prevent GGTI-2417-dependent increase in p27 levels (FIG. 4B), suggesting that GGTI-2417 stabilizes rather than induces p27. Immunofluorescent staining revealed that in MDA-MB-468 cells, nuclear levels of p27 increased 6-fold in response to GGTI-2417, whereas the cytosolic p27 levels were not affected significantly (FIGS. 4C and D).

Figure 5A:
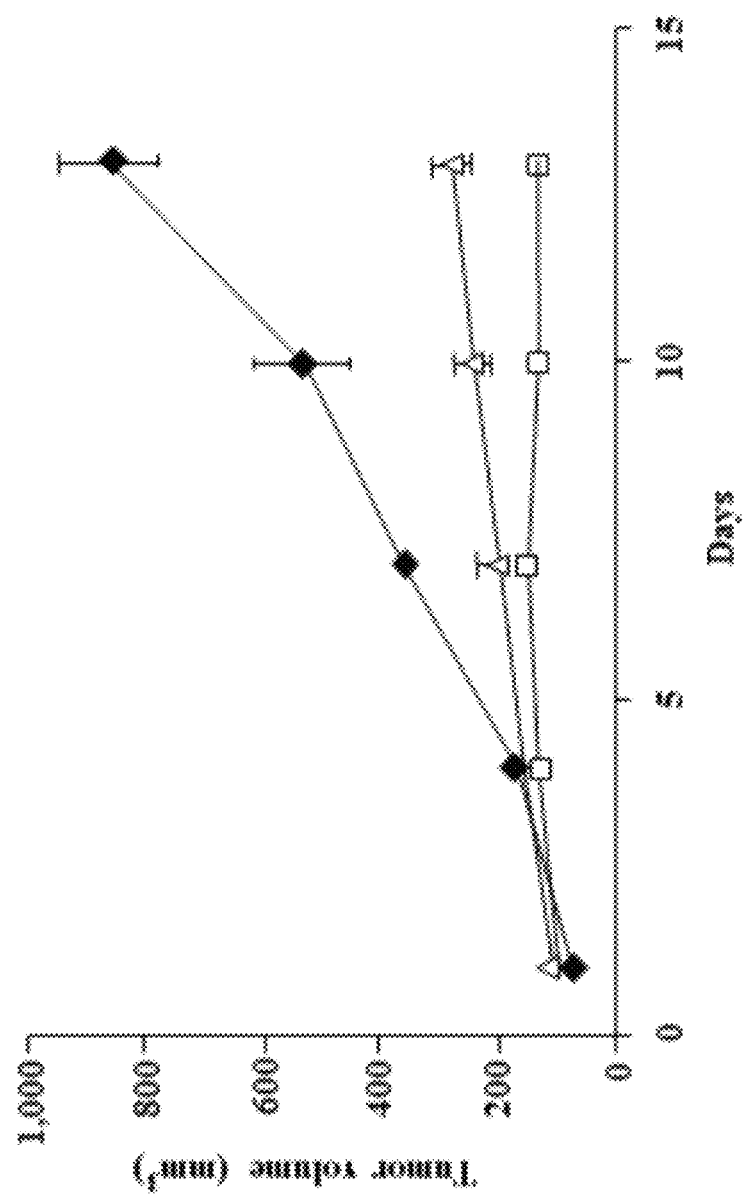
FIGS. 5A-D show that GGTI-2418 significantly inhibits the growth of breast tumor xenografts and induces regression of ErbB2-driven mammary tumors in transgenic mice.

GGTI-2418 significantly inhibits the growth of breast tumors in two animal models. To determine whether GGTI-2418 inhibits tumor growth in nude mice, human MDA-MB-231 breast cancer cells were implanted orthotopically in the mammary fat pads. Tumors from vehicle-treated mice grew to an average size of 860±87 mm$^3$. In contrast, tumors from mice treated with 100 mg/kg GGTI-2418 daily or 200 mg/kg every 3$^{rd}$ day grew to only average tumor sizes of 139±17 or 276±26 mm$^3$, respectively (FIG. 5A), corresponding to a tumor growth inhibition of 94% and 77%, respectively ($p<0.005$ for both). Treatment with 100 mg/kg GGTI-2417 daily resulted in growth inhibition of 76% ($p<0.005$) (data not shown). Taken together these data clearly indicate that GGTI-2418 potently inhibits the growth of breast tumor xenografts with either daily or intermittent dosing. It should be noted that in one aspect, GGTase inhibiting compounds (e.g., GGTI-2418) can be administered to a mammal in an effective amount from about 50 mg/kg/day to about 200 mg/kg/day. In one aspect, an effective amount is about 100 mg/kg/day. In another aspect, the term "administer" means to provide or prescribe a medication comprising a GGTase inhibiting compound or delivering the GGTase inhibiting compound by any suitable route of administration (e.g., orally, intravenous, intramuscular, transdermal, transmucosal, topical, enteral, parenteral, and inhalation) to a mammal, a tumor, or tumor cells (e.g., breast cancer cells).

Figure 5B:
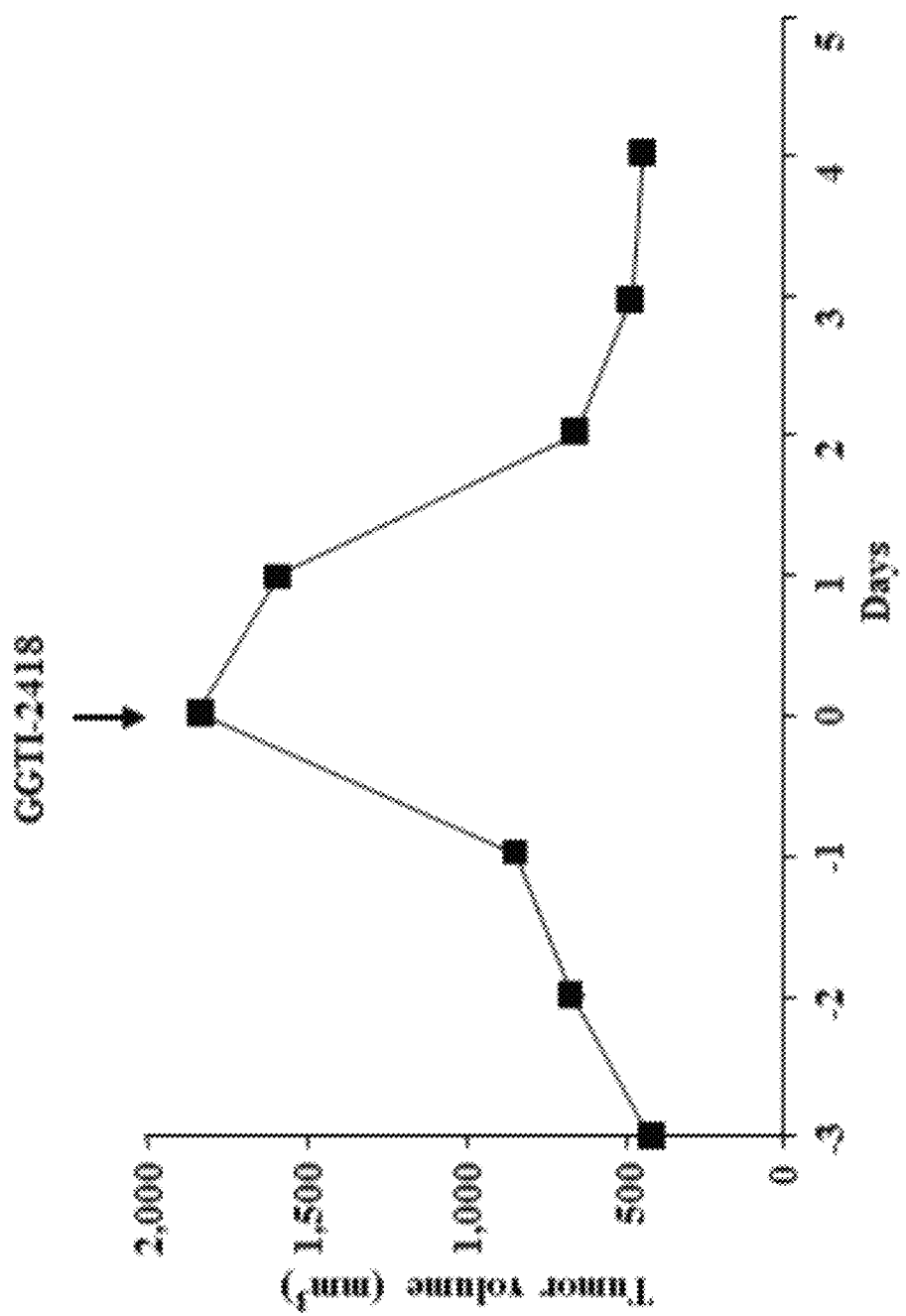
Figure 5C:
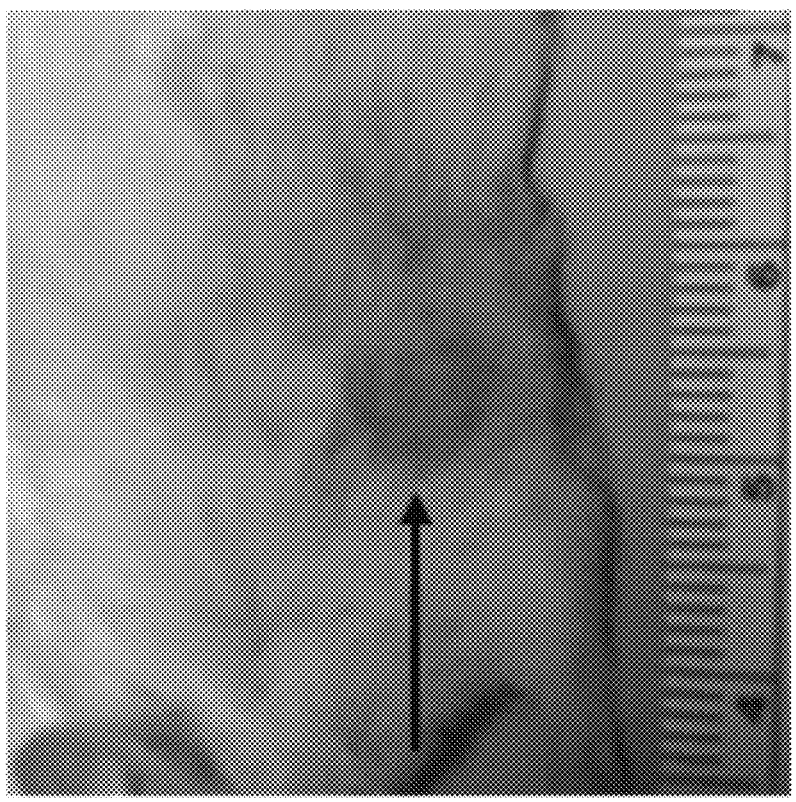
Figure 5C:
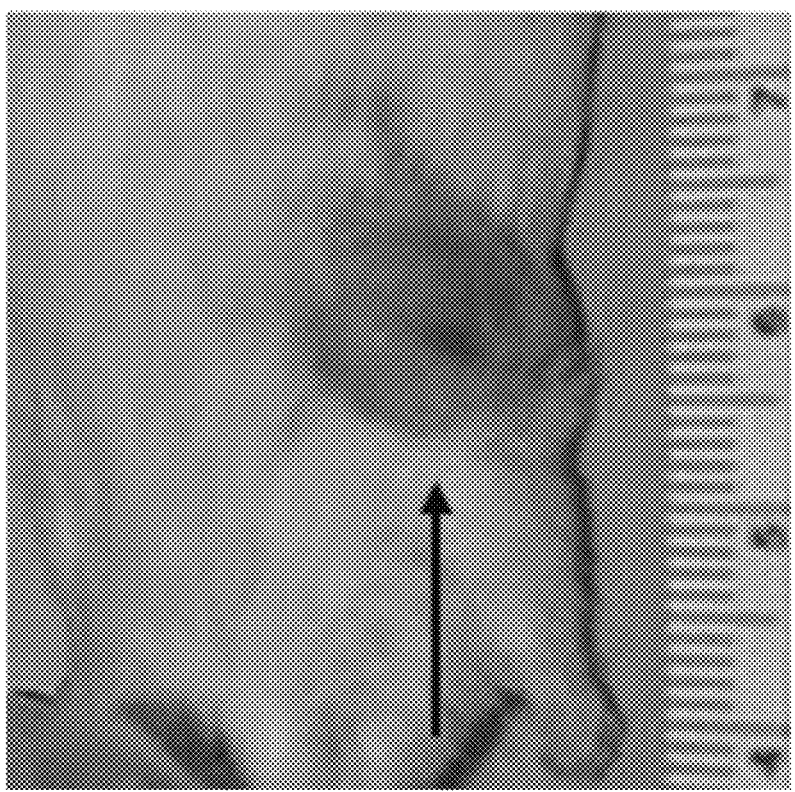

To determine whether GGTI-2418 is also effective in an entirely different tumor model, ErbB2-transgenic mice were used, which developed mammary tumors ranging in size from 818 to 3,903 mm$^3$ (FIG. 8). In the absence of treatment, tumor growth was rapid at 103±12 mm$^3$ per day. In contrast, treatment with GGTI-2418 at 100 mg/kg/day not only halted tumor growth, but actually induced massive tumor regression within a few days. FIGS. 5B and C show a representative example of a tumor that decreased by 76% following GGTI-2418 treatment. The degree of regression was independent of the size of the tumor before initiation of treatment: In 7 mice with a total of 17 tumors, treatment with 100 mg/kg GGTI-2418 resulted in tumor regression between 34 and 100%, with an average of 60±4% (S.E.M.) (FIG. 8).

Figure 5D:
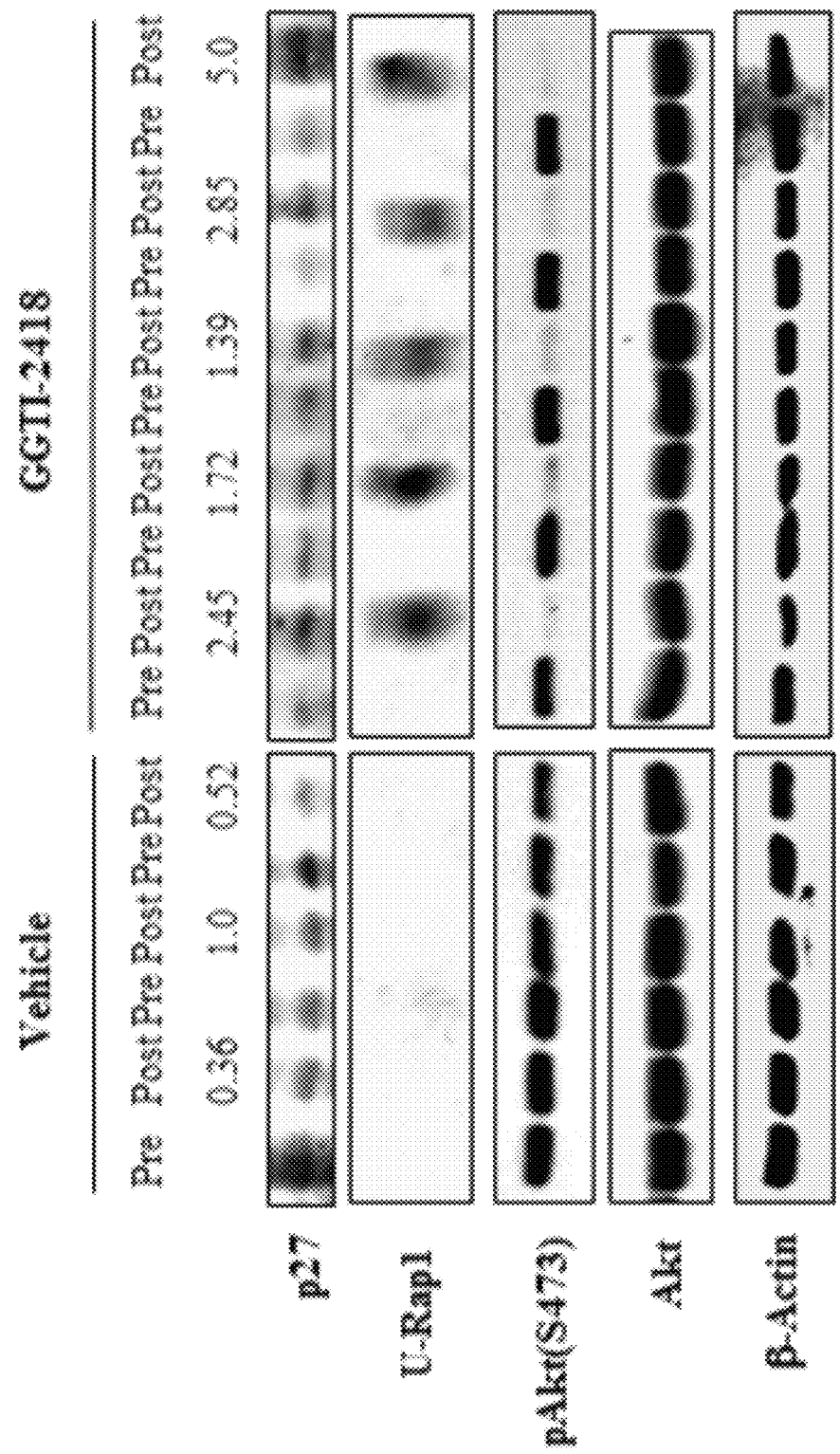

To evaluate whether the tumor regression described above was associated with changes in p27 levels as well as the known molecular targets of GGTI-2418, Rap 1 and phospho-Akt in vivo, tumor biopsies were performed in several mice before (pre) and after initiation of GGTI-2418 treatment (post). As shown in FIG. 5D, GGTI-2418 therapy inhibited the geranylgeranylation of Rap1 and caused a dramatic decrease in S473 phosphorylation of Akt. Most importantly, in three out of three vehicle-treated mice, p27 levels decreased or did not change during tumor progression, whereas in five out of five GGTI-treated mice, p27 levels were upregulated between 1.4- and 5-fold.

Rho proteins are over-expressed and/or persistently activated in breast cancer, and this is associated with poor patient prognosis. One possible mechanism by which Rho proteins may contribute to breast cancer oncogenesis is by down-regulating the levels of the CDK inhibitor p27. Indeed, in cultured cells Rho proteins have been shown to decrease the protein levels of p27, possibly through a mechanism involving the protein kinase ROCK, a downstream effector of Rho proteins. The fact that low p27 levels are associated with poor prognosis, resistance to chemotherapy and shorter life expectancy of breast cancer patients supports the hypothesis that Rho proteins may contribute to breast cancer oncogenesis by keeping p27 levels persistently low. Inhibition of geranylgeranylation, which is required for Rho function, results in a robust upregulation of p27.

The inventors show for the first time that GGTIs are shown to upregulate p27 levels, and that p27 is required for GGTI-2417 to induce breast tumor cell death. Using either p27 null cells or p27 siRNA, in cells expressing no or very little p27, GGTI-2417 was unable to induce cell death. On the other hand, GGTI-2417 could still induce hypophosphorylation of pRb and inhibit the proliferation of cells expressing very little or no p27 (FIGS. 3B and 3E), indicating that GGTI-mediated $G_0/G_1$ arrest may depend on molecules other than p27. GGTI-induced increase in nuclear p27 function is required for the ability of GGTI-2417 to induce breast tumor cell death. p27 protein levels and subcellular distribution are regulated by reversible phosphorylation on multiple sites. Phosphorylation at Thr187 by Cdk2/cyclin E in $G_1$ creates a so-called phosphodegron that is recognized by the SCF$^{Skp2}$ ubiquitin ligase, which recruits p27 to ubiquitin-dependent proteolysis. GGTI-2417 inhibits Thr187 phosphorylation of p27 by Cdk2 and its subsequent degradation. A previous report demonstrated that a first generation GGTI analog, GGTI-298, inhibits Cdk2 activity. Adnane, J., et al., p21(WAF1/CIP1) is upregulated by the geranylgeranyltransferase I inhibitor GGTI-298 through a transforming growth factor β- and Sp1-responsive element: involvement of the small GTPase RhoA, Mol Cell Biol 18:6962-70 (1998). However, it has been a puzzling problem how p27 can be effectively phosphorylated by Cdk2, which is bound to, and kept inactive by p27. Recently, a possible explanation to this conundrum has been provided by the finding that p27 (SEQ ID NO. 1) is phosphorylated on Tyr74 and Tyr88, which partially activates p27-bound Cdk2/cyclin E complexes and thus appears to convert p27 from a Cdk2 inhibitor to a Cdk2 substrate. Chu, I., et al., p27 phosphorylation by Src regulates inhibition of cyclin E-cdk2, Cell 128:281-294 (2007); Grimmler, M., et al., Cdk-inhibitory activity and stability of p27Kip1 are directly regulated by oncogenic tyrosine kinases, Cell 128:269-280 (2007). Considering these recent data, the present results (see FIG. 4A) are also consistent with the idea that GGTI-2417 downregulates Tyr phosphorylation of p27. Whether this contributes to the even greater loss of phosphorylation in Thr187 remains to be determined.

Furthermore, GGTI-2417 did not increase cytoplasmic p27. This is important, since more recent data suggest that cytoplasmic p27 has tumor-promoting activities. For example, in cancer cells persistently activated Akt phosphorylates cytoplasmic p27 at both Thr198 and Thr157, which stabilizes p27 and prevents its re-import to the nucleus, respectively. RNAi experiments suggest that cytoplasmic p27 increases cell migration, survival and tumorigenicity of human glioma cells, and human metastatic melanoma cells have high levels of cytoplasmic p27. Most strikingly, a p27 mutant unable to bind cyclins or Cdks, accumulates in the cytoplasm and has oncogenic properties in a mouse knock-in model. Together, these data suggest that both expression levels and subcellular distribution of p27 are important for tumor prognosis and therapeutic strategies. Given that GGTI-2417 also prevented Akt activation (see FIG. 5D), it is possible that GGTI-2417 may be able to promote p27's cytoplasmic degradation and/or relocation into the nucleus.

Breast tumors aberrantly overexpress several genes that are known to activate Rho proteins that in turn downregulate p27. For example, the receptor tyrosine kinases EGFR and ErbB2 are overexpressed in a large number of breast cancers. These receptors activate Ras which in turn activates Rho proteins. Our findings that GGTI-2418 suppresses the growth in nude mice of MDA-MB-231 breast tumors (which contain a K-Ras mutation), and that GGTI-2418 causes tumor regression in a transgenic animal model where breast tumors are driven by ErbB2, further support our hypothesis that GGTIs will have potent antitumor activity in breast cancers where signaling pathways lead to activation of Rho and subsequent downregulation of p27. This is also consistent with recent studies demonstrating that ErbB2 antibodies such as herceptin modulate p27 via multiple signaling pathways.

p27 is important for cell death and that tumors must keep their nuclear level low to survive. This is consistent with the fact that low levels of p27 are required for assembling Cyclin D/Cdk 4,6 complexes whereas high levels inhibit Cdk activities. Taken together, the inventors have identified inhibition of p27 phosphorylation and the subsequent accumulation of nuclear p27 as a key mediator in the mechanism of GGTI antitumor activity and demonstrate that inhibition of protein geranylgeranylation may be an effective approach to breast cancer therapy. The recent finding that a targeted deletion of the β subunit of GGTase I reduces tumor formation and improves the survival of mice with Kras-expressing lung tumors further validates GGTIs as potential antitumor agents. This, coupled with the fact that GGTI-2418 causes significant regression of breast tumors driven by ErbB2, a prevalent poor prognostic factor in this disease, gives strong support to evaluating GGTIs in breast cancer patients whose tumors contain low levels of nuclear p27 and/or express high levels of ErbB2.

It will be seen that the advantages set forth above, and those made apparent from the foregoing description, are efficiently attained and since certain changes may be made in the above construction without departing from the scope of the description, it is intended that all matters contained in the foregoing description or shown in the accompanying drawings shall be interpreted as illustrative and not in a limiting sense.

It is also to be understood that the following claims are intended to cover all of the generic and specific features of the claims herein described, and all statements of the scope of the claims which, as a matter of language, might be said to fall therebetween.

REFERENCES

It should also be understood that any and all references cited in this specification are hereby incorporated in their entirety.

1. Adnane, J., F. A. Bizouarn, Y. Qian, A. D. Hamilton, and S. M. Sebti. 1998. p21(WAF1/CIP1) is upregulated by the geranylgeranyltransferase I inhibitor GGTI-298 through a transforming growth factor_- and Sp1-responsive element: involvement of the small GTPase RhoA. Mol. Cell. Biol. 18:6962-6970.
2. Alkarain, A., R. Jordan, and J. Slingerland. 2004. p27 deregulation in breast cancer: prognostic significance and implications for therapy. J. Mammary Gland Biol. Neoplasia 9:67-80.
3. Badache, A., and A. Gonçalves. 2006. The ErbB2 signaling network as a target for breast cancer therapy. J. Mammary Gland Biol. Neoplasia 11:13-25.
4. Bagui, T. K., R. J. Jackson, D. Agrawal, and W. J. Pledger. 2000. Analysis of cyclin D3-cdk4 complexes in fibroblasts expressing and lacking p27(kip1) and p21(cip1). Mol. Cell. Biol. 20:8748-8757.
5. Barbareschi, M. 1999. p27 expression, a cyclin dependent kinase inhibitor in breast carcinoma. Adv. Clin. Pathol. 3:119-127.
6. Besson, A., H. C. Hwang, S. Cicero, S. L. Donovan, M. Gurian-West, D. Johnson, B. E. Clurman, M. A. Dyer, and J. A. Roberts. 2007. Discovery of an oncogenic activity in p27Kip1 that causes stem cell expansion and a multiple tumor phenotype. Genes Dev. 21:1731-1746.
7. Blain, S. W., H. I. Scher, C. Cordon-Cardo, and A. Koff. 2003. p27 as a target for cancer therapeutics. Cancer Cell 3:111-115.
8. Borriello, A., V. Cucciolla, A. Oliva, V. Zappia, and F. Della Ragione. 2007. p27Kip1 metabolism: a fascinating labyrinth. Cell Cycle 6:1053-1061.
9. Burbelo, P., A. Wellstein, and R. G. Pestell. 2004. Altered Rho GTPase signaling pathways in breast cancer cells. Breast Cancer Res. Treat. 84: 43-48.
10. Cariou, S., C. Catzavelos, and J. M. Slingerland. 1998. Prognostic implications of expression of the cell cycle inhibitor protein p27Kip1. Breast Cancer Res. Treat. 52:29-41.
11. Catzavelos, C., N. Bhattacharya, Y. C. Ung, J. A. Wilson, L. Roncari, C. Sandhu, P. Shaw, H. Yeger, I. Morava-Protzner, L. Kapusta, E. Franssen, K. I. Pritchard, and J. M. Slingerland. 1997. Decreased levels of the cellcycle inhibitor p27Kip1 protein: prognostic implications in primary breast cancer. Nat. Med. 3:227-230.
12. Chu, I., J. Sun, A. Arnaout, H. Kahn, W. Hanna, S. Narod, P. Sun, C.-K. Tan, L. Hengst, and J. M. Slingerland. 2007. p27 phosphorylation by Src regulates inhibition of cyclin E-cdk2. Cell 128:281-294.
13. Chu, I. M., L. Hengst, and J. M. Slingerland. 2008. The Cdk inhibitor p27 in human cancer: prognostic potential and relevance to anticancer therapy. Nat. Rev. Cancer 8:253-267.
14. Coleman, M. L., R. M. Densham, D. R. Croft, and M. F. Olson. 2006. Stability of p21Waf1/Cip1 CDK inhibitor protein is responsive to RhoA-mediated regulation of the actin cytoskeleton. Oncogene 25:2708-2716.
15. Coleman, M. L., C. J. Marshall, and M. F. Olson. 2004. RAS and RHO GTPases in G1-phase cell-cycle regulation. Nat. Rev. Mol. Cell Biol. 5:355-366.
16. Croft, D. R., and M. F. Olson. 2006. The Rho GTPase effector ROCK regulates cyclin A, cyclin D1, and p27Kip1 levels by distinct mechanisms. Mol. Cell. Biol. 26:4612-4627.
17. Dan, H. C., K. Jiang, D. Coppola, A. Hamilton, S. V. Nicosia, S. M. Sebti, and J. Q. Cheng. 2004. Phosphatidylinositol-3-OH kinase/AKT and survivin pathways as critical targets for geranylgeranyltransferase I inhibitor-induced apoptosis. Oncogene 23:706-715.
18. Denicourt, C., C. C. Saenz, B. Datnow, X.-S. Cui, and S. F. Dowdy. 2007. Relocalized p27Kip1 tumor suppressor functions as a cytoplasmic metastatic oncogene in melanoma. Cancer Res. 67:9238-9243.
19. Drexler, H. C. 2003. The role of p27Kip1 in proteasome inhibitor induced apoptosis. Cell Cycle 2:438-441.
20. Falsetti, S. C., D.-A. Wang, H. Peng, D. Carrico, A. D. Cox, C. J. Der, A. D. Hamilton, and S. M. Sebti. 2007. Geranylgeranyltransferase I inhibitors target RalB to inhibit anchorage-dependent growth and induce apoptosis, and RalA to inhibit anchorage-independent growth. Mol. Cell. Biol. 27: 8003-8014.
21. Fritz, G., and B. Kaina. 2006. Rho GTPases: promising cellular targets for novel anticancer drugs. Curr. Cancer Drug Targets 6:1-14.

22. Gelb, M. H., L. Brunsveld, C. A. Hrycyna, S. Michaelis, F. Tamanoi, W. C. Van Voorhis, and H. Waldmann. 2006. Therapeutic intervention based on protein prenylation and associated modifications. Nat. Chem. Biol. 2:518-528.
23. Grimmler, M., Y. Wang, T. Mund, Z. Cilenšek, E.-M. Keidel, M. B. Waddell, H. Jäkel, M. Kullmann, R. W. Kriwacki, and L. Hengst. 2007. Cdk-inhibitory activity and stability of p27Kip1 are directly regulated by oncogenic tyrosine kinases. Cell 128:269-280.
24. Han, S., K. Park, H. Y. Kim, M. S. Lee, H. J. Kim, and Y. D. Kim. 1999. Reduced expression of p27Kip1 protein is associated with poor clinical outcome of breast cancer patients treated with systemic chemotherapy and is linked to cell proliferation and differentiation. Breast Cancer Res. Treat. 55:161-167.
25. Hara, T., T. Kamura, K. Nakayama, K. Oshikawa, S. Hatakeyama, and K.-I. Nakayama. 2001. Degradation of p27Kip1 at the G0-G1 transition mediated by a Skp2-independent ubiquitination pathway. J. Biol. Chem. 276:48937-48943.
26. Hirai, A., S. Nakamura, Y. Noguchi, T. Yasuda, M. Kitagawa, I. Tatsuno, T. Oeda, K. Tahara, T. Terano, S. Narumiya, L. D. Kohn, and Y. Saito. 1997. Geranylgeranylated Rho small GTPase(s) are essential for the degradation of p27Kip1 and facilitate the progression from G1 to S phase in growth stimulated rat FRTL-5 cells. J. Biol. Chem. 272:13-16.
27. Hu, W., C. J. Bellone, and J. J. Baldassare. 1999. RhoA stimulates p27(Kip) degradation through its regulation of cyclin E/CDK2 activity. J. Biol. Chem. 274:3396-3401.
28. Ishida, N., T. Hara, T. Kamura, M. Yoshida, K. Nakayama, and K. I. Nakayama. 2002. Phosphorylation of p27Kip1 on serine 10 is required for its binding to CRM1 and nuclear export. J. Biol. Chem. 277:14355-14358.
29. Ishida, N., M. Kitagawa, S. Hatakeyama, and K.-I. Nakayama. 2000. Phosphorylation at serine 10, a major phosphorylation site of p27(Kip1), increases its protein stability. J. Biol. Chem. 275:25146-25154.
30. Kamura, T., T. Hara, M. Matsumoto, N. Ishida, F. Okumura, S. Hatakeyama, M. Yoshida, K. Nakayama, and K. I. Nakayama. 2004. Cytoplasmic ubiquitin ligase KPC regulates proteolysis of p27(Kip1) at G1 phase. Nat. Cell Biol. 6:1229-1235.
31. Kaufmann, S. H., S. Desnoyers, Y. Ottaviano, N. E. Davidson, and G. G. Poirier. 1993. Specific proteolytic cleavage of poly(ADP-ribose) polymerase: an early marker of chemotherapy-induced apoptosis. Cancer Res. 53:3976-3985.
32. Kossatz, U., J. Vervoorts, I. Nickeleit, H. A. Sundberg, J. S. C. Arthur, M. P. Manns, and N. P. Malek. 2006. C-terminal phosphorylation controls the stability and function of p27Kip1. EMBO J. 25:5159-5170.
33. Le, X. F., F. Pruefer, and R. C. Bast, Jr. 2005. HER2-targeting antibodies modulate the cyclin-dependent kinase inhibitor p27Kip1 via multiple signaling pathways. Cell Cycle 4:87-95.
34. Lerner, E. C., Y. Qian, M. A. Blaskovich, R. D. Fossum, A. Vogt, J. Sun, A. D. Cox, C. J. Der, A. D. Hamilton, and S. M. Sebti. 1995. Ras CAAX peptidomimetic FTI-277 selectively blocks oncogenic Ras signaling by inducing cytoplasmic accumulation of inactive Ras-Raf complexes. J. Biol. Chem. 270:26802-26806.
35. Lerner, E. C., Y. Qian, A. D. Hamilton, and S. M. Sebti. 1995. Disruption of oncogenic K-Ras4B processing and signaling by a potent geranylgeranyltransferase I inhibitor. J. Biol. Chem. 270:26770-26773.
36. Liang, J., J. Zubovitz, T. Petrocelli, R. Kotchetkov, M. K. Connor, K. Han, J. H. Lee, S. Ciarallo, C. Catzavelos, R. Beniston, E. Franssen, and J. M. Slingerland. 2002. PKB/Akt phosphorylates p27, impairs nuclear import of p27 and opposes p27-mediated G1 arrest. Nat. Med. 8:1153-1160.
37. Min, Y. H., J. W. Cheong, J. Y. Kim, J. I. Eom, S. T. Lee, J. S. Hahn, Y. W. Ko, and M. H. Lee. 2004. Cytoplasmic mislocalization of p27Kip1 protein is associated with constitutive phosphorylation of Akt or protein kinase B and poor prognosis in acute myelogenous leukemia. Cancer Res. 64:5225-5231.
38. Peng, H., D. Carrico, V. That, M. Blaskovich, C. Bucher, E. E. Pusateri, S. M. Sebti, and A. D. Hamilton. 2006. Synthesis and evaluation of potent, highly-selective, 3-aryl-piperazinone inhibitors of protein geranylgeranyltransferase—I. Org. Biomol. Chem. 4:1768-1784.
39. Ridley, A. J. 2004. Rho proteins and cancer. Breast Cancer Res. Treat. 84:13-19.
40. Sebti, S. M. 2005. Protein farnesylation: implications for normal physiology, malignant transformation, and cancer therapy. Cancer Cell 7:297-300.
41. Sebti, S. M., and C. J. Der. 2003. Opinion: searching for the elusive targets of farnesyltransferase inhibitors. Nat. Rev. Cancer. 3:945-951.
42. Sebti, S. M., and A. D. Hamilton. 2000. Farnesyltransferase and geranylgeranyltransferase I inhibitors and cancer therapy: lessons from mechanism and bench-to-bedside translational studies. Oncogene 19:6584-6593.
43. Sherr, C. J., and J. M. Roberts. 1999. CDK inhibitors: positive and negative regulators of G1-phase progression. Genes Dev. 13:1501-1512.
44. Shin, I., F. M. Yakes, F. Rojo, N. Y. Shin, A. V. Bakin, J. Baselga, and C. L. Arteaga. 2002. PKB/Akt mediates cell-cycle progression by phosphorylation of p27(Kip1) at threonine 157 and modulation of its cellular localization. Nat. Med. 8:1145-1152.
45. Sjogren, A.-K., K. M. E. Andersson, m. Liu, B. A. Cutts, C. Karlsson, A. M. Wahlstrom, M. Dalin, C. A. Weinbaum, P. J. Casey, A. Tarkowski, B. Swolin, S. G. Young, and M. O. Bergo. 2007. GGTase-1 deficiency reduces tumor formation and improves survival in mice with K-Ras-induced lung cancer. J. Clin. Investig. 117:1294-1304.
46. Sun, J., M. A. Blaskovich, D. Knowles, Y. Qian, J. Ohkanda, R. D. Bailey, A. D. Hamilton, and S. M. Sebti. 1999. Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. Cancer Res. 59:4919-4926.
47. Sun, J., Y. Qian, Z. Chen, J. Marfurt, A. D. Hamilton, and S. M. Sebti. 1999. The geranylgeranyltransferase I inhibitor GGTI-298 induces hypophosphorylation of retinoblastoma and partner switching of cyclin-dependent kinase inhibitors. A potential mechanism for GGTI-298 antitumor activity. J. Biol. Chem. 274:6930-6934.
48. Vargo-Gogola, T., and J. M. Rosen. 2007. Modeling breast cancer: one size does not fit all. Nat. Rev. Cancer 7:659-672.
49. Viglietto, G., M. L. Motti, P. Bruni, R. M. Melillo, A. D'Alessio, D. Califano, F. Vinci, G. Chiappetta, P. Tsichlis, A. Bellacosa, A. Fusco, and M. Santoro. 2002. Cytoplasmic relocalization and inhibition of the cyclin-dependent kinase inhibitor p27Kip1 by PKB/Akt-mediated phosphorylation in breast cancer. Nat. Med. 8:1136-1144.

50. Vogt, A., J. Sun, Y. Qian, A. D. Hamilton, and S. M. Sebti. 1997. The geranylgeranyltransferase-I inhibitor GGTI-298 arrests human tumor cells in G0/G1 and induces p21(WAF1/CIP1/SDI1) in a p53-independent manner. J. Biol. Chem. 272:27224-27229.
51. Walker, K., and M. F. Olson. 2005. Targeting Ras and Rho GTPases as opportunities for cancer therapeutics. Curr. Opin. Genet. Dev. 15:62-68.
52. Weber, J. D., W. Hu, S. C. Jefcoat, Jr., D. M. Raben, and J. J. Baldassare. 1997. Ras-stimulated extracellular signal-related kinase 1 and RhoA activities coordinate platelet-derived growth factor-induced G1 progression through the independent regulation of cyclin D1 and p27. J. Biol. Chem. 272:32966-32971.
53. Wu, F. Y., S. E. Wang, M. E. Sanders, I. Shin, F. Rojo, J. Baselga, and C. L. Arteaga. 2006. Reduction of cytosolic p27Kip1 inhibits cancer cell motility, survival, and tumorigenicity. Cancer Res. 66:2162-2172.
54. Zhang, F. L., and P. J. Casey. 1996. Protein prenylation: molecular mechanisms and functional consequences. Annu. Rev. Biochem. 65:241-269.

SEQ ID NO. 1

MSNVRVSNGS PSLERMDARQ AEHPKPSACR NLFGPVDHEE

LTRDLEKHCR DMEEASQRKW NFDFQNHKPL EGKYEWQEVE

KGSLPEFYYR PPRPPKGACK VPAQESQDVS GSRPAAPLIG

APANSEDTHL VDPKTDPSDS QTGLAEQCAG IRKRPATDDS

STQNKRANRT EENVSDGSPN AGSVEQTPKK PGLRRRQT

---

What is claimed is:

1. A method of treating breast cancer in a subject in need thereof, comprising:
    assaying a breast cancer sample comprising breast cancer cells from the subject for nuclear p27 levels;
    comparing the nuclear p27 levels to a control level of nuclear p27;
    detecting breast cancer cells in the breast cancer sample having nuclear p27 levels that are below control levels of nuclear p27; and
    administering a therapeutically effective amount of GGTI-2418 to the subject.

2. The method of claim 1, wherein the effective amount is 100 mg/kg/day.

3. The method of claim 1, wherein the effective amount is 200 mg/kg every third day.

4. The method of claim 1, wherein the administration is performed by intraperitoneal injection.

* * * * *

SEQUENCE LISTING

<160> NUMBER OF SEQ ID NOS: 2

<210> SEQ ID NO 1
<211> LENGTH: 198
<212> TYPE: PRT
<213> ORGANISM: homo sapiens

<400> SEQUENCE: 1

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 2
<211> LENGTH: 4
<212> TYPE: PRT
<213> ORGANISM: artificial sequence
<220> FEATURE:
<223> OTHER INFORMATION: terminating tetrapeptide sequence of proteins

```
-continued

<220> FEATURE:
<221> NAME/KEY: misc_feature
<222> LOCATION: (4)..(4)
<223> OTHER INFORMATION: Xaa can be any naturally occurring amino acid

<400> SEQUENCE: 2

Cys Ala Ala Xaa
1
```